(12) United States Patent
Gunn

(10) Patent No.: US 9,226,851 B2
(45) Date of Patent: Jan. 5, 2016

(54) MEMS CHECK VALVE CHIP AND METHODS

(71) Applicant: ALCON RESEARCH, LTD., Fort Worth, TX (US)

(72) Inventor: Nicholas Max Gunn, Newport Beach, CA (US)

(73) Assignee: Novartis AG, Basel (CH)

( * ) Notice: Subject to any disclaimer, the term of this patent is extended or adjusted under 35 U.S.C. 154(b) by 300 days.

(21) Appl. No.: 13/975,307

(22) Filed: Aug. 24, 2013

(65) Prior Publication Data

US 2015/0057592 A1 Feb. 26, 2015

(51) Int. Cl.
*A61M 5/00* (2006.01)
*A61F 9/007* (2006.01)
*A61B 3/16* (2006.01)

(52) U.S. Cl.
CPC .............. *A61F 9/00781* (2013.01); *A61B 3/16* (2013.01)

(58) Field of Classification Search
CPC .............. A61F 9/00781; A61F 9/0017; A61F 9/00761; A61F 9/007; A61M 27/00; A61M 2210/0612; A61B 5/0084
USPC ........... 604/8, 9, 28; 606/107–108; 623/1–12; 424/422, 423
See application file for complete search history.

(56) References Cited

U.S. PATENT DOCUMENTS

| 3,441,245 A | 4/1969 | Holland et al. |
|---|---|---|
| 3,759,289 A | 9/1973 | DeWall |
| 4,089,329 A | 5/1978 | Couvillon, Jr. et al. |
| 4,206,762 A | 6/1980 | Cosman |
| 4,457,757 A | 7/1984 | Molteno |
| 4,604,087 A | 8/1986 | Joseph |
| 4,656,827 A | 4/1987 | Puillet |
| 4,750,901 A | 6/1988 | Molteno |
| 4,869,282 A | 9/1989 | Sittler et al. |
| 4,922,913 A | 5/1990 | Waters, Jr. et al. |
| 5,005,577 A | 4/1991 | Frenkel |
| 5,071,408 A | 12/1991 | Ahmed |
| 5,083,742 A | 1/1992 | Wylie et al. |
| 5,171,213 A | 12/1992 | Price, Jr. |

(Continued)

FOREIGN PATENT DOCUMENTS

| DE | 4438201 | 5/1996 |
|---|---|---|
| EP | 0102747 | 3/1984 |

(Continued)

OTHER PUBLICATIONS

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

(Continued)

*Primary Examiner* — Philip R Wiest
(74) *Attorney, Agent, or Firm* — Kenneth D. Bassinger

(57) ABSTRACT

A MEMS check valve chip is described. The chip comprises a first side and an opposing second side, an outlet port extending from the first side to the second side, and a flexible outlet membrane anchored to the first side to overlie the outlet port. The flexible outlet membrane includes an outlet aperture and a sealing portion, and the sealing portion is movable between a closed position inhibiting fluid flow through the outlet aperture and an open position wherein the sealing portion displaces into the outlet port to permit fluid flow through the outlet aperture.

12 Claims, 10 Drawing Sheets

(56) References Cited

U.S. PATENT DOCUMENTS

| | | |
|---|---|---|
| 5,178,604 A | 1/1993 | Baerveldt et al. |
| 5,179,953 A | 1/1993 | Kursar |
| 5,192,265 A | 3/1993 | Drake et al. |
| 5,326,345 A | 7/1994 | Price, Jr. |
| 5,397,300 A | 3/1995 | Baerveldt et al. |
| 5,466,233 A | 11/1995 | Weiner et al. |
| 5,476,445 A | 12/1995 | Baerveldt et al. |
| 5,558,629 A | 9/1996 | Baerveldt et al. |
| 5,573,646 A | 11/1996 | Saito et al. |
| 5,626,558 A | 5/1997 | Suson |
| 5,655,898 A | 8/1997 | Hashimoto et al. |
| 5,681,275 A | 10/1997 | Ahmed |
| 5,702,618 A | 12/1997 | Saaski et al. |
| 5,707,643 A | 1/1998 | Ogura et al. |
| 5,891,097 A | 4/1999 | Saito et al. |
| 5,910,110 A | 6/1999 | Bastable |
| 5,968,058 A | 10/1999 | Richter et al. |
| 6,007,511 A | 12/1999 | Prywes |
| 6,047,698 A | 4/2000 | Magidson et al. |
| 6,048,328 A | 4/2000 | Haller et al. |
| 6,050,970 A | 4/2000 | Baerveldt |
| 6,090,062 A | 7/2000 | Sood et al. |
| 6,186,974 B1 | 2/2001 | Allan et al. |
| 6,251,090 B1 | 6/2001 | Avery et al. |
| 6,261,256 B1 | 7/2001 | Ahmed |
| 6,383,160 B1 | 5/2002 | Madsen |
| 6,443,893 B1 | 9/2002 | Schnakenberg et al. |
| 6,447,449 B1 | 9/2002 | Fleischman et al. |
| 6,453,940 B1 | 9/2002 | Tipton et al. |
| 6,468,283 B1 | 10/2002 | Richter et al. |
| 6,533,733 B1 | 3/2003 | Ericson et al. |
| 6,544,208 B2 | 4/2003 | Ethier et al. |
| 6,554,208 B1 | 4/2003 | Venuto, Sr. |
| 6,579,235 B1 | 6/2003 | Abita et al. |
| 6,589,198 B1 | 7/2003 | Soltanpour et al. |
| 6,626,858 B2 | 9/2003 | Lynch et al. |
| 6,682,500 B2 | 1/2004 | Soltanpour et al. |
| 6,712,764 B2 | 3/2004 | Jeffries et al. |
| 6,719,750 B2 | 4/2004 | Varner et al. |
| 6,736,791 B1 | 5/2004 | Tu et al. |
| 6,749,568 B2 | 6/2004 | Fleischman et al. |
| 6,855,770 B2 | 2/2005 | Pinchuk et al. |
| 6,939,299 B1 | 9/2005 | Petersen et al. |
| 6,976,982 B2 | 12/2005 | Santini, Jr. et al. |
| 7,137,952 B2 | 11/2006 | Leonardi et al. |
| 7,169,106 B2 | 1/2007 | Fleischman et al. |
| 7,226,540 B2 | 6/2007 | Rodgers et al. |
| 7,252,006 B2 | 8/2007 | Tai et al. |
| 7,304,334 B2 | 12/2007 | Agarwal et al. |
| 7,354,416 B2 | 4/2008 | Quiroz-Mercado et al. |
| 7,364,564 B2 | 4/2008 | Sniegowski et al. |
| 7,384,550 B2 | 6/2008 | Rodgers et al. |
| 7,409,863 B2 | 8/2008 | Bateman et al. |
| 7,431,709 B2 | 10/2008 | Pinchuk et al. |
| 7,488,303 B1 | 2/2009 | Haffner et al. |
| 7,544,176 B2 | 6/2009 | Rodgers et al. |
| 7,612,328 B2 | 11/2009 | Kaiser |
| 7,648,465 B2 | 1/2010 | Gordon |
| 7,670,310 B2 | 3/2010 | Yaron et al. |
| 7,756,559 B2 | 7/2010 | Abreu |
| 7,824,699 B2 | 11/2010 | Ralph et al. |
| 7,850,637 B2 | 12/2010 | Lynch et al. |
| 7,857,782 B2 | 12/2010 | Tu et al. |
| 7,862,531 B2 | 1/2011 | Yaron et al. |
| 7,867,186 B2 | 1/2011 | Haffner et al. |
| 8,070,708 B2 | 12/2011 | Rottenberg et al. |
| 8,182,435 B2 | 5/2012 | Dacquay et al. |
| 8,206,440 B2 | 6/2012 | Guarnieri |
| 8,257,295 B2 | 9/2012 | Rickard et al. |
| 8,419,673 B2 | 4/2013 | Rickard |
| 8,549,925 B2 | 10/2013 | Tai et al. |
| 8,753,305 B2 * | 6/2014 | Field .................. A61F 9/00781 604/9 |
| 8,814,820 B2 | 8/2014 | Bergheim et al. |
| 2001/0000527 A1 | 4/2001 | Yaron et al. |
| 2002/0019607 A1 | 2/2002 | Bui |
| 2002/0049374 A1 | 4/2002 | Abreu |
| 2002/0087111 A1 | 7/2002 | Ethier et al. |
| 2002/0099359 A1 | 7/2002 | Santini, Jr. et al. |
| 2002/0103412 A1 | 8/2002 | Trimmer |
| 2002/0139947 A1 | 10/2002 | Wang |
| 2002/0143284 A1 | 10/2002 | Tu et al. |
| 2002/0175191 A1 | 11/2002 | Joshi et al. |
| 2002/0193674 A1 | 12/2002 | Fleischman et al. |
| 2003/0014036 A1 | 1/2003 | Varner et al. |
| 2003/0078487 A1 | 4/2003 | Jeffries et al. |
| 2003/0139729 A1 | 7/2003 | Stegmann et al. |
| 2003/0225318 A1 | 12/2003 | Montegrande et al. |
| 2004/0013702 A1 | 1/2004 | Glover |
| 2004/0059248 A1 | 3/2004 | Messner et al. |
| 2004/0073137 A1 | 4/2004 | Lloyd et al. |
| 2004/0111050 A1 | 6/2004 | Smedley et al. |
| 2004/0116794 A1 | 6/2004 | Fink et al. |
| 2004/0162545 A1 | 8/2004 | Brown et al. |
| 2004/0186367 A1 | 9/2004 | Fresco |
| 2004/0193095 A1 | 9/2004 | Shadduck |
| 2004/0254438 A1 | 12/2004 | Chuck et al. |
| 2004/0254517 A1 | 12/2004 | Quiroz-Mercado et al. |
| 2005/0049578 A1 | 3/2005 | Tu et al. |
| 2005/0159660 A1 | 7/2005 | Montegrande et al. |
| 2005/0175494 A1 | 8/2005 | Shibamoto et al. |
| 2005/0184003 A1 | 8/2005 | Rodgers et al. |
| 2005/0271704 A1 | 12/2005 | Tu et al. |
| 2005/0273033 A1 | 12/2005 | Grahn et al. |
| 2006/0041220 A1 | 2/2006 | Boukhny et al. |
| 2006/0131350 A1 | 6/2006 | Schechter et al. |
| 2007/0019156 A1 | 1/2007 | Fink |
| 2007/0032757 A1 | 2/2007 | Medow et al. |
| 2007/0077270 A1 | 4/2007 | Wen |
| 2007/0106199 A1 | 5/2007 | Krivoy et al. |
| 2007/0106200 A1 | 5/2007 | Levy |
| 2007/0109117 A1 | 5/2007 | Heitzmann et al. |
| 2007/0123767 A1 | 5/2007 | Montegrande et al. |
| 2007/0129623 A1 | 6/2007 | Fleischmann et al. |
| 2007/0156079 A1 | 7/2007 | Brown |
| 2007/0212397 A1 | 9/2007 | Roth |
| 2007/0255262 A1 | 11/2007 | Haase |
| 2008/0015421 A1 | 1/2008 | Penner |
| 2008/0027478 A1 | 1/2008 | Connors et al. |
| 2008/0066815 A1 | 3/2008 | Anderson |
| 2008/0077127 A1 | 3/2008 | Gao et al. |
| 2008/0097276 A1 | 4/2008 | Bertrand et al. |
| 2008/0125691 A1 | 5/2008 | Yaron et al. |
| 2008/0129486 A1 | 6/2008 | Jeckelmann et al. |
| 2008/0147021 A1 | 6/2008 | Jani |
| 2008/0228127 A1 | 9/2008 | Burns et al. |
| 2008/0257915 A1 | 10/2008 | Wold |
| 2009/0069648 A1 | 3/2009 | Irazqui et al. |
| 2009/0076367 A1 | 3/2009 | Sit et al. |
| 2009/0143713 A1 | 6/2009 | Van Dam et al. |
| 2009/0159826 A1 | 6/2009 | Poulton et al. |
| 2009/0227933 A1 | 9/2009 | Karageozian |
| 2009/0240215 A1 | 9/2009 | Humayun et al. |
| 2009/0275924 A1 | 11/2009 | Lattanzio et al. |
| 2009/0277206 A1 | 11/2009 | Laufenberg et al. |
| 2009/0312742 A1 | 12/2009 | Pang et al. |
| 2010/0010416 A1 | 1/2010 | Juan, Jr. et al. |
| 2010/0042209 A1 | 2/2010 | Guarnieri |
| 2010/0121248 A1 | 5/2010 | Yu et al. |
| 2010/0121348 A1 | 5/2010 | van der Burg et al. |
| 2010/0174272 A1 | 7/2010 | Weiner |
| 2010/0222769 A1 | 9/2010 | Meng et al. |
| 2010/0222770 A1 | 9/2010 | Gordon et al. |
| 2010/0234717 A1 | 9/2010 | Wismer |
| 2010/0253167 A1 | 10/2010 | Charnley et al. |
| 2010/0305550 A1 | 12/2010 | Meng et al. |
| 2011/0046536 A1 | 2/2011 | Stegmann et al. |
| 2011/0071454 A1 | 3/2011 | Dos Santos et al. |
| 2011/0071456 A1 | 3/2011 | Rickard |
| 2011/0071458 A1 | 3/2011 | Rickard |
| 2011/0071505 A1 | 3/2011 | Rickard et al. |
| 2011/0211974 A1 | 9/2011 | Harper |
| 2011/0248671 A1 | 10/2011 | Dos Santos et al. |
| 2012/0121449 A1 | 5/2012 | Borst et al. |

(56) References Cited

U.S. PATENT DOCUMENTS

| | | |
|---|---|---|
| 2012/0177510 A1 | 7/2012 | Delong et al. |
| 2013/0150779 A1 | 6/2013 | Field |
| 2013/0204177 A1 | 8/2013 | Field et al. |
| 2013/0211311 A1 | 8/2013 | Field |

FOREIGN PATENT DOCUMENTS

| | | |
|---|---|---|
| EP | 1195523 | 4/2002 |
| EP | 1917987 | 5/2008 |
| EP | 2427097 | 3/2012 |
| JP | 03049775 | 3/1991 |
| WO | 9303665 | 3/1993 |
| WO | 9803665 | 1/1998 |
| WO | 9803809 | 1/1998 |
| WO | 9938470 A2 | 8/1999 |
| WO | 9938470 A3 | 10/1999 |
| WO | 0029770 | 5/2000 |
| WO | 0037128 | 6/2000 |
| WO | 0174427 | 10/2001 |
| WO | 0194784 | 12/2001 |
| WO | 02056758 | 7/2002 |
| WO | 03001991 | 1/2003 |
| WO | 03102632 | 12/2003 |
| WO | 2004014218 | 2/2004 |
| WO | 2005079204 | 9/2005 |
| WO | 2005088417 | 9/2005 |
| WO | 2007127305 | 11/2007 |
| WO | 2007136993 | 11/2007 |
| WO | 2008060649 | 5/2008 |
| WO | 2008061043 A2 | 5/2008 |
| WO | 2008084350 A2 | 7/2008 |
| WO | 2008094672 A2 | 8/2008 |
| WO | 2008061043 A3 | 9/2008 |
| WO | 2008084350 A3 | 10/2008 |
| WO | 2008094672 A3 | 11/2008 |
| WO | 2009010799 | 1/2009 |
| WO | 2009026499 | 2/2009 |
| WO | 2009049686 | 4/2009 |
| WO | 2009081031 A2 | 7/2009 |
| WO | 2009081031 A3 | 9/2009 |
| WO | 2010093945 | 8/2010 |
| WO | 2010129446 | 11/2010 |
| WO | 2011034727 | 3/2011 |
| WO | 2011034738 | 3/2011 |
| WO | 2011034740 | 3/2011 |
| WO | 2011034742 A2 | 3/2011 |
| WO | 2011035218 | 3/2011 |
| WO | 2011034742 A3 | 5/2011 |
| WO | 2012012017 | 1/2012 |
| WO | 2013085894 A2 | 6/2013 |
| WO | 2013085895 A1 | 6/2013 |
| WO | 2013090231 A1 | 6/2013 |
| WO | 2013123142 A1 | 8/2013 |

OTHER PUBLICATIONS

Driot et al.; "Ocular pharmacokinetics of fluocinolone acetonide after RetisertTM intravitreal implantation in rabbits over a 1-year period"; J. Ocular Pharm; 20; 3;pp. 269-275.

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.

Glybina et al.; "Neuroprotective properties of fluocinolone acetonide chronically delivered into the vitreous of albino RCS rats"; IVOS; 47; ARVO e-Abstract 1028.

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

International Searching Authority, International Preliminary Report on Patentability of the International Searching Authority, PCT/US2013/042351, Nov. 25, 2014, 8 pages.

International Searching Authority, International Preliminary Report on Patentability, PCT/US2013/033717, Oct. 1, 2014, 9 pages.

International Searching Authority, International Search Report and Written Opinion of the International Searching Authority, PCT/US2013/026066, Apr. 17, 2013, 8 pages.

International Searching Authority, International Search Report and Written Opinion of the International Searching Authority, PCT/US2013/033717, Jul. 9, 2013, 14 pages.

International Searching Authority, Invitation to Pay Additional Fees and, Where Applicable, Protest Fee (Partial Search Report attached), PCT/US2012/067741, Apr. 2, 2013, 6 pages.

International Searching Authority, Search Report and Written Opinion of the International Searching Authority PCT US2010/047605; Dec. 16, 2010.

International Searching Authority, Search Report and Written Opinion of the International Searching Authority PCT/US2010/047612; Dec. 21, 2010.

International Searching Authority, Search Report and Written Opinion of the International Searching Authority PCT/US2012/067747 dated Apr. 2, 2013.

International Searching Authority, Search Report and Written Opinion of the International Searching Authority PCT/US2012/068878 dated Apr. 3, 2013.

International Searching Authority, Search Report and Written Opinion of the International Searching Authority, PCT/US2010/033329, Jul. 13, 2010, 14 pages.

International Searching Authority, Search Report and Written Opinion of the International Searching Authority, PCT/US2010/047429, Nov. 1, 2010, 15 pages.

International Searching Authority, Search Report and Written Opinion of the International Searching Authority, PCT/US2010/047600, Dec. 14, 2010, 13 pages.

International Searching Authority, Search Report and Written Opinion of the International Searching Authority, PCT/US2010/049424, Nov. 26, 2010, 15 pages.

International Searching Authority, Search Report and Written Opinion of the International Searching Authority, PCT/US2011/036742, Aug. 17, 2011, 2 pages.

International Searching Authority, Search Report and Written Opinion of the International Searching Authority, PCT/US2013/042351, May 9, 2013, 11 pages.

Kuppermann B D et al., 2006, "Efficacy and safety of a novel intravitreous deIDSamethasone drug-delivery system after applicator or incisional placement in patients with macular edema", IOVS, 47 ARVO E-Abs 5913.

Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.

Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.

Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.

McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.

Miyamoto H et al., 1997, Biodegradable scleral implant for intravitreal controlled release of fluconazole, Curr Eye Res, 16(9), 930-935.

Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.

Mruthyunjaya P et al., 2003, "An intravitreal sustained release fluocinolone acetonide device to treat severe eIDSperimental uveitis", IOVS, 44, ARVO E-Abs 4215.

(56) References Cited

OTHER PUBLICATIONS

Neagu Cristina R.; "A Medical Microactuator Based on an Electrochemical Principle"; Thesis at the Twente University, the Netherlands, Enschede; Aug. 28, 1998; pp. 1-162.
Nisar, et al.; MEMS-Based Micropumps in Drug Delivery and Biomedical Applications; ScienceDirect; Sensors and Actuators B 130; pp. 917-942 (2008).
Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.
Ratanapakorn T et al., 2005, "Helical intravitreal triamcinolone implant: An eIDSplanation survival study", IVOS 46 E-Abs 484.
Rego MGR et al., 2004, "In vitro evaluation of sustained-release intravitreal deIDSamethasone implants", IOVS, 45 E-Abs 5060.
Sakurai E et al., 2001, "Scleral plug of biodegradable polymers containing ganciclovir for eIDSperimental cytomegalovirus retinitis", IOVS, 42(9), 2043-2048.
Saloomeh Saati M.D., et al.; "Mini Drug Pump for Ophthalmic Use"; Trans Am Ophthalmol Soc 2009; 107; pp. 60-71.
Schnakenberg, U., et al, "Initial Investigations on Systems for Measuring Intraocular Pressure," Sensors and Actuators, 2000, p. 287-291, vol. 85, Elsevier Science B.V., Germany.
See R F et al., 2006, "Safety and drug release profile of injectable intravitreal sustained-release fluocinolone acetonide device", IOVS, 47, ARVO E-Abs 5119.
Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.
Stemme et al.; "A Valveless Diffuser/Nozzle-Based Fluid Pump"; ScienceDirect; Sensors and Actuators A, 39; pp. 159-167 (1993).
Tano R et al., 2005, Helical intravitreal implant: surgical method development and outcomes, IOVS, 46, ARVO E-Abs 483.
Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.
Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.
Varner S E et al., 2003, "Development of a minimally invasive intravitreal implant for drug delivery", IOVS, 44, ARVO E-Abs 4214.
Walter, Peter; Intraocular Pressure Sensor: Where Are We—Where Will We Go? Journal Graefe's Archive for Clinical and Experimental Ophthalmology; Publisher Springer Berline/Heidelberg; ISSN 0721-832X (Print) 1435-702X (Online); Issue vol. 240, No. 5/May 2002 DOI 10.1007/s00417-002-0474-y; pp. 335-336; Subject Collection Medicine.
Weiner A L, 2007, "Drug Delivery Systems in Ophthalmic Applications, In: Ocular Therapeutics; Eye on New Discoveries; T. Yorio, A. Clark, M.WaIDS, Eds, Elsevier Press/Academic Press, New York", pp. 7-43.
Yasukawa T et al., 2001, "Biodegradable scleral plugs for vitreoretinal drug delivery", Adv. Drug Del Rev., 52(1), 25-36.

\* cited by examiner

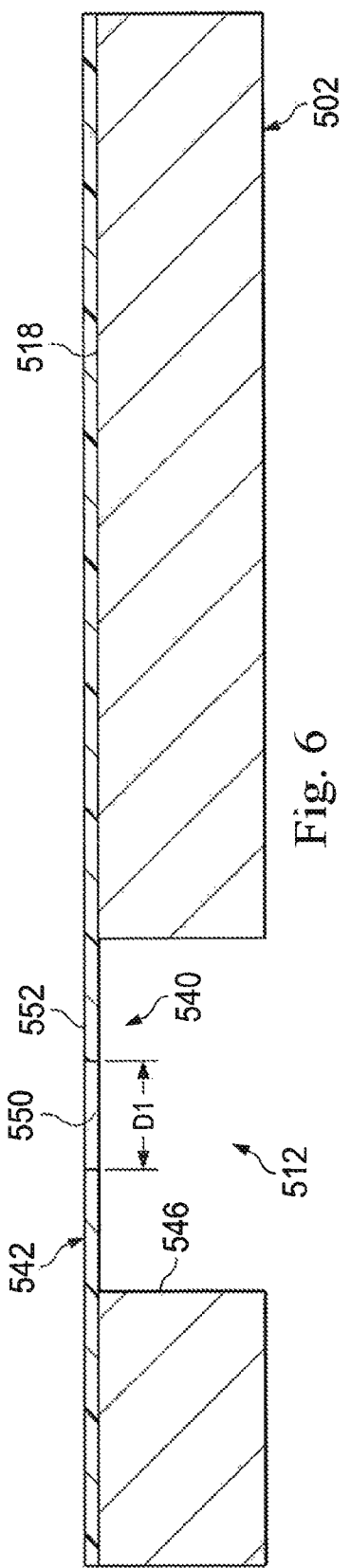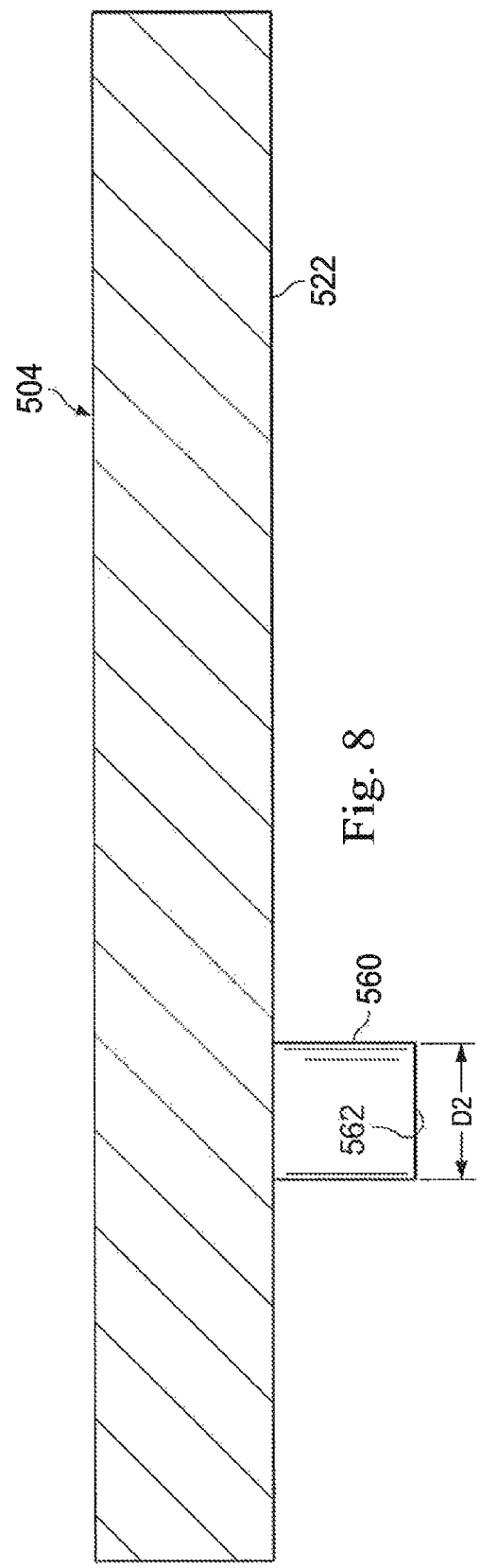

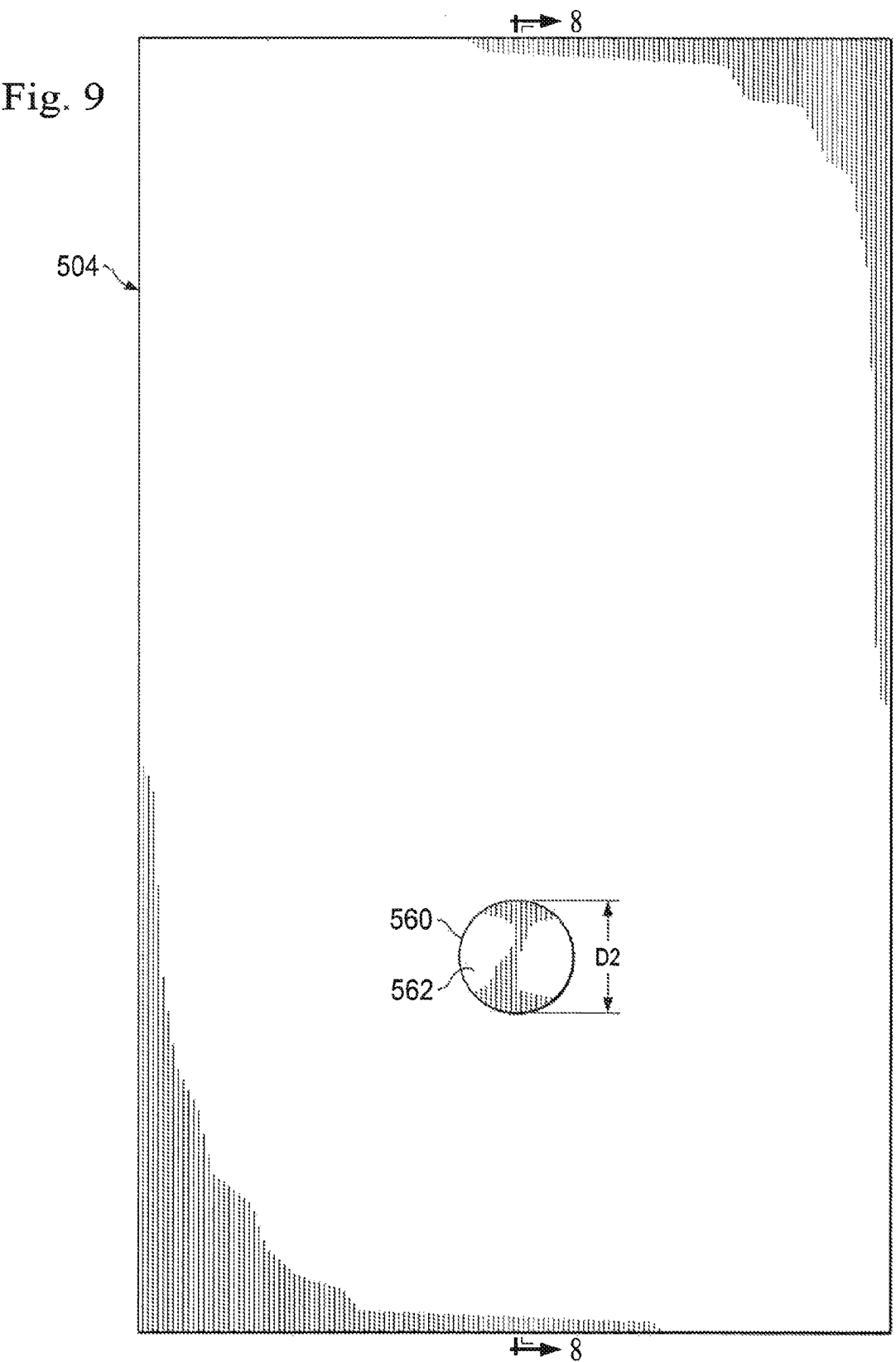

MEMS CHECK VALVE CHIP AND METHODS

BACKGROUND

The present disclosure relates generally to valves and associated systems and methods. In some instances, embodiments of the present disclosure are configured to be part of an intraocular pressure (IOP) control system for use in ophthalmic treatments.

Glaucoma, a group of eye diseases affecting the retina and optic nerve, is one of the leading causes of blindness worldwide. Most forms of glaucoma result when the IOP increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior segment of the eye includes the structures that cause elevated IOP which may lead to glaucoma. Aqueous humor fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber 170. The angle of the anterior chamber 170, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. The drainage device allows fluid to flow from the anterior chamber of the eye to a drainage site, relieving pressure in the eye and thus lowering IOP. In order to provide desired treatments to patients, it may be important to regulate the flow of aqueous humor through the drainage device. Drainage devices with flow regulation devices, however, may be large and unwieldy when implanted in the eye. Such devices may present various complications, including, without limitation, discomfort to the patient and tissue irritation. Therefore, it may be desirable to provide flow regulation devices in a smaller package more suitable for implantation in the eye.

The system and methods disclosed herein overcome one or more of the deficiencies of the prior art.

SUMMARY

In one exemplary aspect, this disclosure is directed to a MEMS check valve chip for use in the treatment of an ocular condition. In one aspect, the MEMS check valve comprises a first side and an opposing second side, an outlet port extending from the first side to the second side, and a flexible outlet membrane disposed on the first side to overlie the outlet port. In one aspect, the outlet membrane includes at least one outlet aperture sized to permit fluid flow therethrough and a sealing portion that is movable between a closed position inhibiting fluid flow through the outlet aperture and an open position. In one aspect, the sealing portion in an open condition displaces into the outlet port and toward the second side to permit fluid flow through the outlet aperture from the first side to the second side.

In one exemplary aspect, the present disclosure is directed to an IOP control device for implantation in an eye of a patient. The IOP control device comprises a first chip, a second chip, an inlet valve, and an outlet valve. In one aspect, the first chip includes a first side, an opposing second side, and the outlet port. In one aspect, the outlet port extends from the first side to the second side and is sized to permit fluid flow therethrough from the first side to the second side. In one aspect, the second chip includes an inner side and an outer side, and the first chip and the second chip stack to form a fluid flow passageway between the first side of the first chip and the inner side of the second chip. In one aspect, the fluid flow passageway has a fluid flow passageway pressure. In one aspect, the inlet valve comprises a flexible inlet membrane that is movable between a closed position inhibiting fluid flow and an open position permitting fluid flow through the inlet valve. In one aspect, the outlet valve comprises a flexible outlet membrane anchored to the first side of the first chip to overlie the outlet port. In one aspect, the outlet membrane includes at least one outlet aperture sized to permit fluid flow therethrough and a sealing portion. In one aspect, the sealing portion is movable between a closed position wherein the sealing portion deflects away from the second side toward fluid flow passageway to inhibit fluid flow through the outlet aperture and an open position wherein the sealing portion displaces into the outlet port toward the second side to permit fluid flow through the outlet aperture.

In another exemplary embodiment, the present disclosure is directed to a method comprising forming an outlet port through a first chip having a first side and an opposing second side, creating a first displaceable member on the first side of the first chip over the outlet member, forming a valve seat on a second chip, and stacking the second chip and the first chip to create a fluid flow passageway therebetween. In one aspect, the outlet port extends through the first chip from the first side to the second side. In one aspect, the first displaceable member has at least one outlet aperture configured to permit the fluid flow therethrough, wherein the first displaceable member displaces into the first chip toward the second side to permit fluid flow through the outlet aperture. In one aspect, the valve seat and the at least one outlet aperture of the first displaceable member are aligned about a central axis extending through the valve seat. In one aspect the first chip and the second chip are stacked to bias the first displaceable member over the valve seat. In one aspect, the fluid flow passageway includes a fluid flow passageway pressure.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 6 is a stylized illustration of a cross-sectional view of a portion of the exemplary valve chip including the exemplary outlet valve shown in FIG. 5.

FIG. 8 is a stylized illustration of a cross-sectional view of a portion of the exemplary actuation chip shown in FIG. 5. The actuation chip includes an exemplary valve seat in accordance with one embodiment of the disclosure.

FIG. 9 is a stylized illustration of a top view of the portion of the valve chip containing the exemplary valve seat shown in FIG. 8.

DETAILED DESCRIPTION

Figure 1:
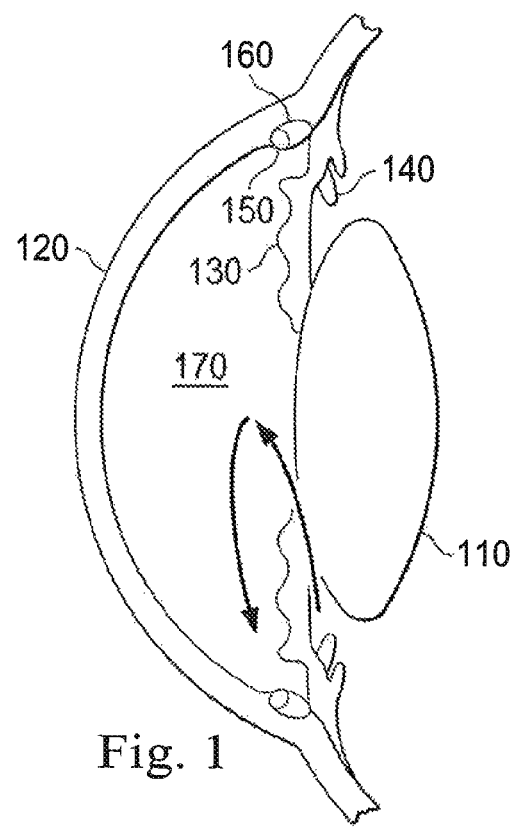
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to a microelectromechanical systems (MEMS) in-to-plane check valve to regulate fluid flow though a flow passageway or chamber. In some instances, embodiments of the present disclosure are configured to be used in the operation of electrolysis-based membrane pumps. In some instances, embodiments of the present disclosure are configured to be part of an IOP control system. Those of skill in the art will realize that the chips and valves disclosed herein may be utilized in alternative applications requiring membrane deflection to selectively open and close a valve.

The MEMS in-to-plane check valve disclosed herein allows flow in one direction, where the direction of flow is into the plane of the substrate or chip. The MEMS in-to-plane check valve may be formed on the side of the chip adjacent to fluid within a flow passageway. The MEMS in-to-plane check valve comprises a flexible membrane (e.g., the outlet membrane 542 described below with reference to FIG. 5) that is pre-biased across a valve seat (e.g., the valve seat 560 described below with reference to FIG. 5). In one embodiment, the flexible membrane of the MEMS in-to-plane check valve may be formed on the same side of a chip as an out-of-plane check valve (i.e., a check valve operable to selectively permit fluid flow out of the body or plane of the chip as it passes the check valve), and the two check valves may restrict fluid flow in opposite directions relative to the flow passageway. In another embodiment, the valve seat of the MEMS in-to-plane check valve may be formed on the same side of a chip as an out-of-plane check valve (i.e., a check valve operable to selectively permit fluid flow out of the body or plane of the chip as it passes the check valve) while the flexible membrane is formed on the same side of a chip as an actuation component, and the two check valves may restrict fluid flow in opposite directions relative to the flow passageway. When used in a MEMS pump system, fluid may flow through an out-of-plane check valve formed on a first side of the chip into the passageway and may be restricted from exiting the passageway through this check valve, but may be permitted to exit the passageway through the MEMS in-to-plane check valve.

Thus, the MEMS in-to-plane check valve disclosed herein allows the fabrication of both inlet and outlet check valves on the same surface of a single substrate or chip (e.g., a silicon wafer). Because the inlet valve and the outlet valve are able to be formed on the same side of the chip, the overall stack size of the pump may be reduced because fewer chips are needed when compared to a device that uses one check valve per chip. In addition, the MEMS in-to-plane check valve can be formed on the same side of the chip as the out-of-plane check valve, which may make chip fabrication less complex (e.g., single-sided wafer processing) and less expensive. The resulting devices may also be less expensive to manufacture because fewer chips and fewer processing steps are required. In addition, the in-to-plane check valves disclosed herein can incorporate a set pressure drop or "cracking pressure" across the valve, which can assist in the clinical management of hypotony associated with glaucoma drainage devices. Thus, the drainage devices using the in-to-plane check valves and chips disclosed herein may be less expensive to manufacture, simpler to manufacture, able to address hypotony, and smaller, thereby making them more comfortable for the patient, potentially easier to implant, and improving the overall clinical result.

Figure 2:
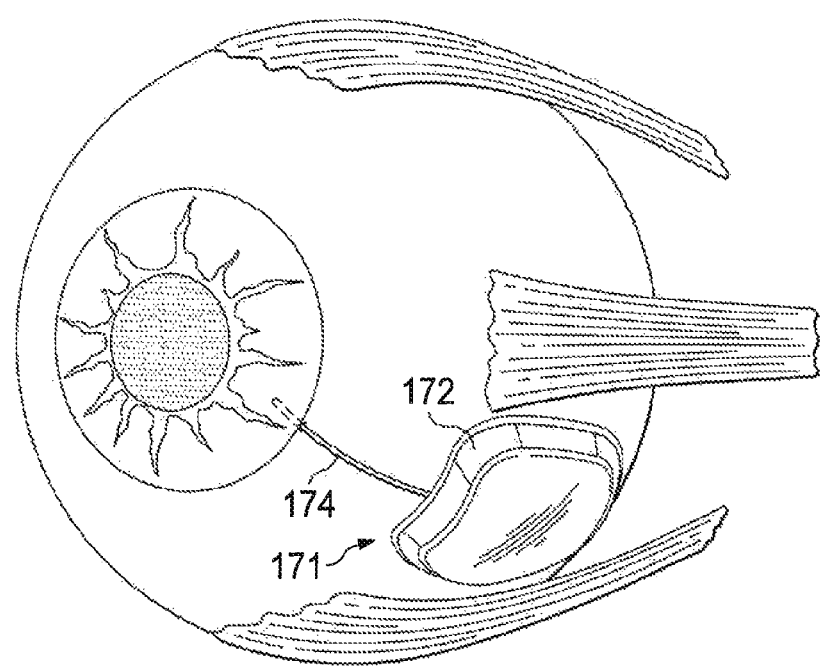
FIG. 2 is an illustration of an exemplary flow-regulating system disposed in the eye in accordance with one embodiment of the present disclosure.

FIG. 2 shows an exemplary implantable system 171 disposed on an eye to treat an ocular condition according to one exemplary aspect of the present disclosure. The implantable system 171 includes a body referred to herein as a plate 172 and a drainage tube 174 that extends from the plate 172. The plate 172 is arranged to carry various components of an IOP control system, and may include a valve, pump, transducers or sensors, a processing system and memory, drug delivery components, a power source, or other components that may be used to either control the implantable system 171 or otherwise treat ocular conditions.

When implanted, the plate 172 may be located in the subconjunctival pocket between the conjunctiva and sclera. It may be generally located on an ocular quadrant commonly used for conventional glaucoma drainage devices with plates; that is, it may be located between neighboring ocular muscles that define the ocular quadrant chosen for implantation. In the pictured embodiment, the plate 172 is configured to fit at least partially within the subconjunctival space and is sized for example within a range between about 15 mm×10 mm to about 30 mm×15 mm. In some embodiments, the plate 172 has a thickness less than about 2 mm thick. For example, in one embodiment, the plate has a thickness of about 1 mm thick. The plate 172 may be curved to approximate the radius of the eye globe. In some embodiments, the plate 172 is rigid and preformed with a curvature suitable to substantially conform to the globe or it may be flexible to conform to the globe. The above dimensions and arrangement are exemplary only, and other sizes and arrangements are contemplated.

The drainage tube 174 is sized to extend from the plate 172 to the anterior chamber of the eye. The drainage tube 174 bridges the anterior chamber and the plate 172 in the subconjunctival pocket to provide an auxiliary flow path for aqueous humor, bypassing the flow-resistive conventional pathway through the trabecular meshwork and shunting aqueous humor directly to a drainage site. In the example shown, the drainage tube 174 is a single tube having a single lumen. Other embodiments include a plurality of drainage tubes or a plurality of lumens cooperating together to permit fluid to flow through the implantable system 171. Aqueous humor may drain through the drainage tube from the anterior chamber to and out of the plate 172 to alleviate elevated intraocular pressure conditions.

Figure 3:
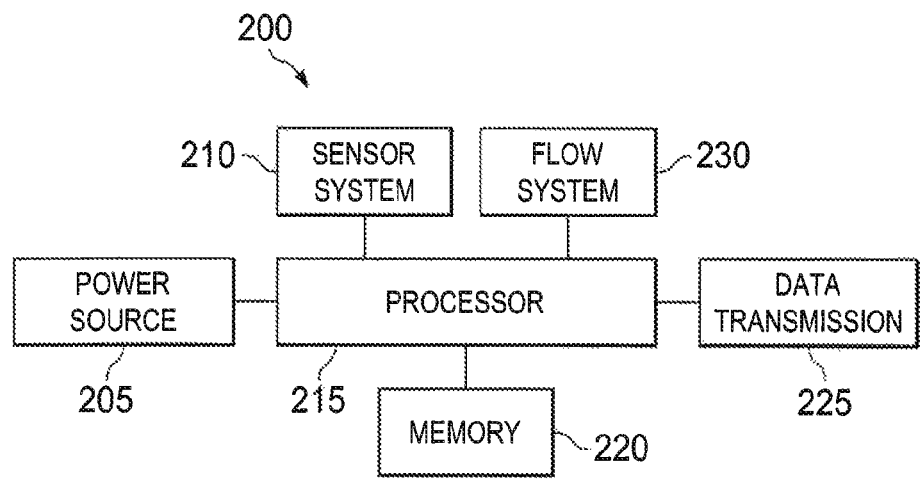
FIG. 3 is a block diagram of an exemplary IOP control system according to the principles of the present disclosure.

FIG. 3 is a schematic diagram of an exemplary IOP control system 200 implantable in an eye of a patient for the treatment of glaucoma or other conditions. A portion or all of the IOP control system 200 may be carried on or may form a part of the implantable system 171. In one embodiment, it is carried on the plate 172. The IOP control system 200 is configured in a manner that provides IOP pressure control. In FIG. 3, the IOP control system 200 includes a power source 205, an IOP sensor system 210, a processor 215, a memory 220, a data transmission module 225, and a flow system 230.

The power source 205, which provides power to the system 200, is typically a rechargeable battery, such as a lithium ion or lithium polymer battery, although other types of batteries may be employed. The power source can be recharged via inductive coupling such as an RFID link or other type of electromagnetic coupling.

The processor 215 is typically an integrated circuit with power, input, and output pins capable of performing logic functions. For example, the processor 215 may perform logic functions based on inputs from the IOP sensor system 210 to determine the current IOP of the eye and operating status of the IOP control system 200. In some embodiments, the processor 215 controls the supply of power from the power source 205 to the flow system 230. In various embodiments, the processor 215 may be a targeted device controller or a microprocessor configured to control more than one component of the device or a combination thereof.

The memory 220, which is typically a semiconductor memory such as RAM, FRAM, or flash memory, interfaces with the processor 215. As such, the processor 215 can write to and read from the memory 220, and perform other common functions associated with managing semiconductor memory. In this manner, a series of IOP readings can be stored in the memory 220.

The data transmission module 225 may employ any of a number of different types of data transmission. For example, in various embodiments, the data transmission module 225 may be an active device such as a radio or a passive device with an antenna capable of wireless communication. The data transmission module 225 may be activated to communicate to a secondary device such as a PDA, cell phone, computer, wrist watch, custom device exclusively for this purpose, remote accessible data storage site (e.g. an internet server, email server, text message server), or other electronic device or service.

The IOP sensor system 210 is described below with reference to FIG. 4, and an embodiment of the flow system 230 is described below with reference to FIGS. 5-12.

Figure 4:
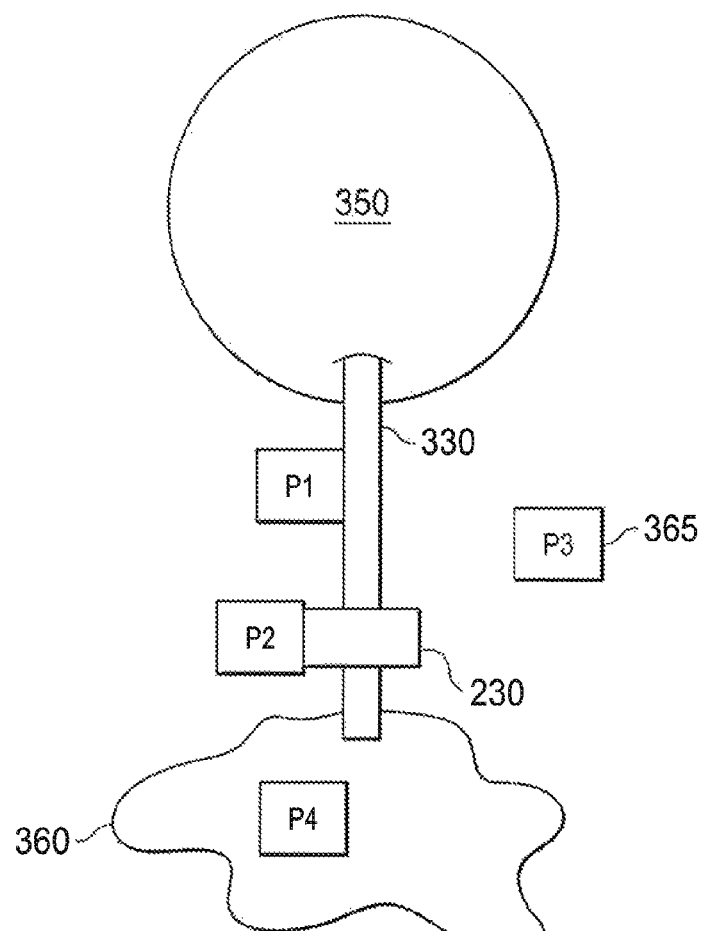
FIG. 4 is a schematic diagram of an exemplary IOP control system according to the principles of the present disclosure disposed within an eye.

FIG. 4 is a diagram of the exemplary IOP sensor system 210 disposed about a representation of an eye, a drainage tube 330, and the flow system 230. The flow system 230 is disposed along, and may form a part of, the drainage tube 330 between the tube end in the anterior chamber 350 and the drainage site 360. The drainage tube 330 may be the same drainage tube 174 discussed with respect to FIG. 2 and drains aqueous humor from the anterior chamber 350 of the eye. The flow system 230 controls the flow of aqueous humor through the tube 330 and may comprise one or more valves, one or more pumps, or a combination of valves and pumps, or other flow devices for regulating or otherwise affecting flow.

In FIG. 4, the exemplary IOP sensor system 210 (shown in FIG. 3) includes four pressure sensors, P1, P2, P3, and P4. The pressure sensor P1 is located in or is in fluidic communication with an anterior chamber 350, the pressure sensor P2 is located to measure intermediate pressures found within the flow system 230, the pressure sensor P3 is located remotely from P1 and P2 in manner to measure atmospheric pressure, and the pressure sensor P4 is located at the drainage site 360 and is arranged to measure drainage pressure, such as a bleb pressure. The pressure sensors P1, P2, P3, and P4 can be any type of pressure sensors suitable for implantation in the eye. They each may be the same type of pressure sensor, or they may be different types of pressure sensors. In some embodiments, the IOP sensor system includes three pressure sensors, corresponding to the sensors P1, P3, and P4 shown in FIG. 4. In particular, the IOP control systems may lack a pressure sensor located to measure intermediate pressures within the valve system (e.g., the pressure sensor P2). In various embodiments, the IOP control system may include any number of pressure sensors or lack pressure sensors altogether.

In some embodiments, the pressure sensor P1 is located in a lumen or tube that is in fluid communication with the anterior chamber, such as the drainage tube 330. In the embodiment shown, the pressure sensor P1 measures the pressure in the tube 330 upstream from the flow system 230 and downstream from the anterior chamber 350. In this manner, pressure sensor P1 measures the pressure in the anterior chamber 350 because the expected measurement discrepancy between the true anterior chamber pressure and that measured by P1 when located in a tube downstream of the anterior chamber is very minimal.

Generally, IOP is a gauge pressure reading—the difference between the absolute pressure in the eye (as measured by P1) and atmospheric pressure (as measured by P3). In one embodiment of the present disclosure, pressure readings are taken by the pressure sensors P1 and P3 simultaneously or nearly simultaneously over time so that the actual IOP can be calculated (as P1−P3 or P1−f(P3), where f(P3) indicates a function of P3). The pressure readings of P1 and P3 can be stored in memory 220 by the processor 215. They can later be read from memory so that actual IOP over time can be interpreted by a physician.

The pressure sensor P4 may be located in a pocket at the drainage site 360, such as a bleb, that generally contains aqueous humor or in communication with such a pocket, via a tube for example, and is in the drainage site 360. The drainage site 360 may be, by way of non-limiting example, in a subconjunctival space, a suprachoroidal space, a subscleral space, a supraciliary space, Schlemm's canal, a collector channel, an episcleral vein, and a uveo-scleral pathway, among other locations in the eye. The difference between the readings taken by the pressure sensor P1 and the pressure sensor P4 (P1−P4) provides an indication of the pressure differential between the anterior chamber 350 and the drainage site 360. In one embodiment, this pressure differential dictates the rate of aqueous humor flow from the anterior chamber 350 to the drainage site 360.

The flow system 230 is configured to control the flow of drainage fluid through the drainage tube 330, and thereby control pressure in the eye, including the IOP. A desired pressure differential can be maintained by controlling the flow through the flow system 230. For example, when IOP is high, the flow system 230 may operate to permit increased flow through the drainage tube 330, and when IOP is low, the flow system 230 may operate to decrease the flow through the drainage tube 330. Likewise, some embodiments of the flow system 230 are configured to monitor and control the flow of drainage fluid to the drainage site 360 or bleb, and thereby control the bleb pressure to maintain a desired fluid flow to the bleb and thereby decrease fibrosis and increase absorption efficiency. To accomplish this, the flow system 230 may be responsive to instructions from the processor 215 based on a pre-programmed treatment protocol or input data received from the pressure sensors P1, P2, P3, and P4, and/or the IOP.

Figure 5:
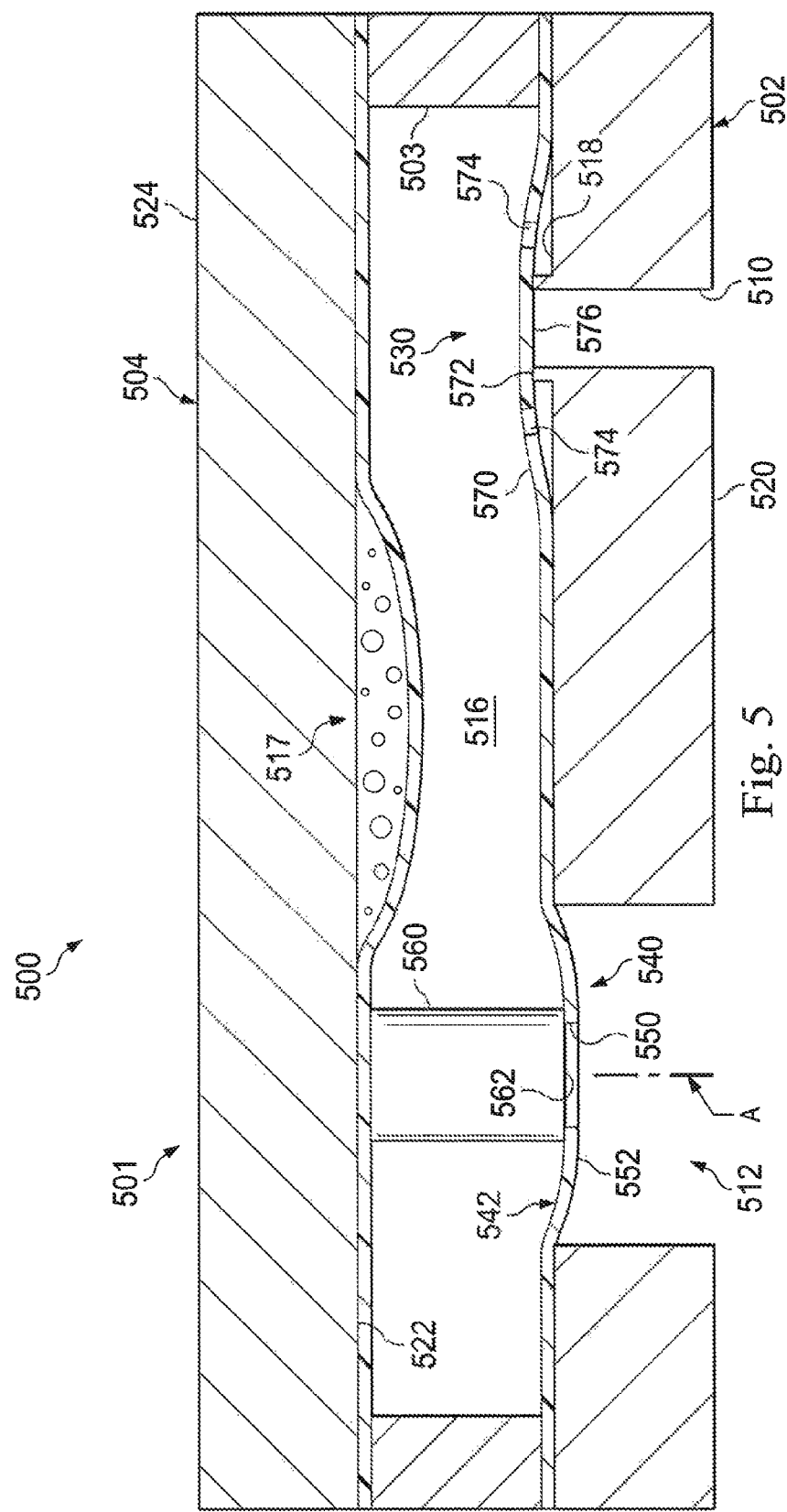
FIG. 5 is a stylized illustration of a cross-sectional view of an exemplary flow system that may be a part of an exemplary IOP control system according to the principles of the present disclosure. The flow system includes an exemplary valve chip and an exemplary actuation chip according to the principles of the present disclosure. The valve chip includes an exemplary inlet valve and an exemplary outlet valve according to the principles of the present disclosure.

FIG. 5 shows a stylized cross-sectional view of an exemplary flow system 500 carried by or forming a part of the plate 172 (shown in FIG. 2). The flow system 500 may be substituted for the flow system 230 and therefore, the discussion above applies equally to the flow system 500. The flow system 500 is configured to selectively allow or block or drive aqueous humor flowing from the anterior chamber 350 through the drainage tube 330 to the drainage site 360 (shown in FIG. 4) or to any subsequent flow control structures such as, by way of non-limiting example, valves, pumps, and/or check valves before entering the drainage site.

The flow system 500 comprises a housing 501 including a valve chip 502, a wall element 503, and an actuation chip 504. In FIG. 5, for illustrative clarity, the valve chip 502 and the actuation chip 504 are shown arranged farther apart from each other than may actually occur. In addition, the flow system 500 comprises an inlet port 510, an outlet port 512, a fluid flow passageway 516 extending between the inlet port 510 and the outlet port 512, and an active component 517. The valve chip 502, the wall element 503, and the actuation chip 504 are shaped and configured to mate and create the fluid flow passageway 516. In some embodiments, the valve chip 502 and the actuation chip 504 are shaped to directly connect to one another to create an enclosed fluid flow passageway without the need for a separate wall element. In this example, the flow system 500 is a pump configured to draw fluid into the fluid flow passageway 516 through the inlet port 510 and expel the fluid from the fluid flow passageway 516 through the outlet port 512. The inlet port 510 may be in fluid communication with the drainage tube 330 (shown in FIG. 4) and is configured to receive aqueous humor flowing from the drainage tube 330 into the fluid flow passageway 516. The outlet port 512 permits fluid to exit the fluid flow passageway 516 for release at a drainage site or for further regulation via additional flow systems. The active component 517 is discussed in further detail below with respect to FIG. 10.

Figure 13:
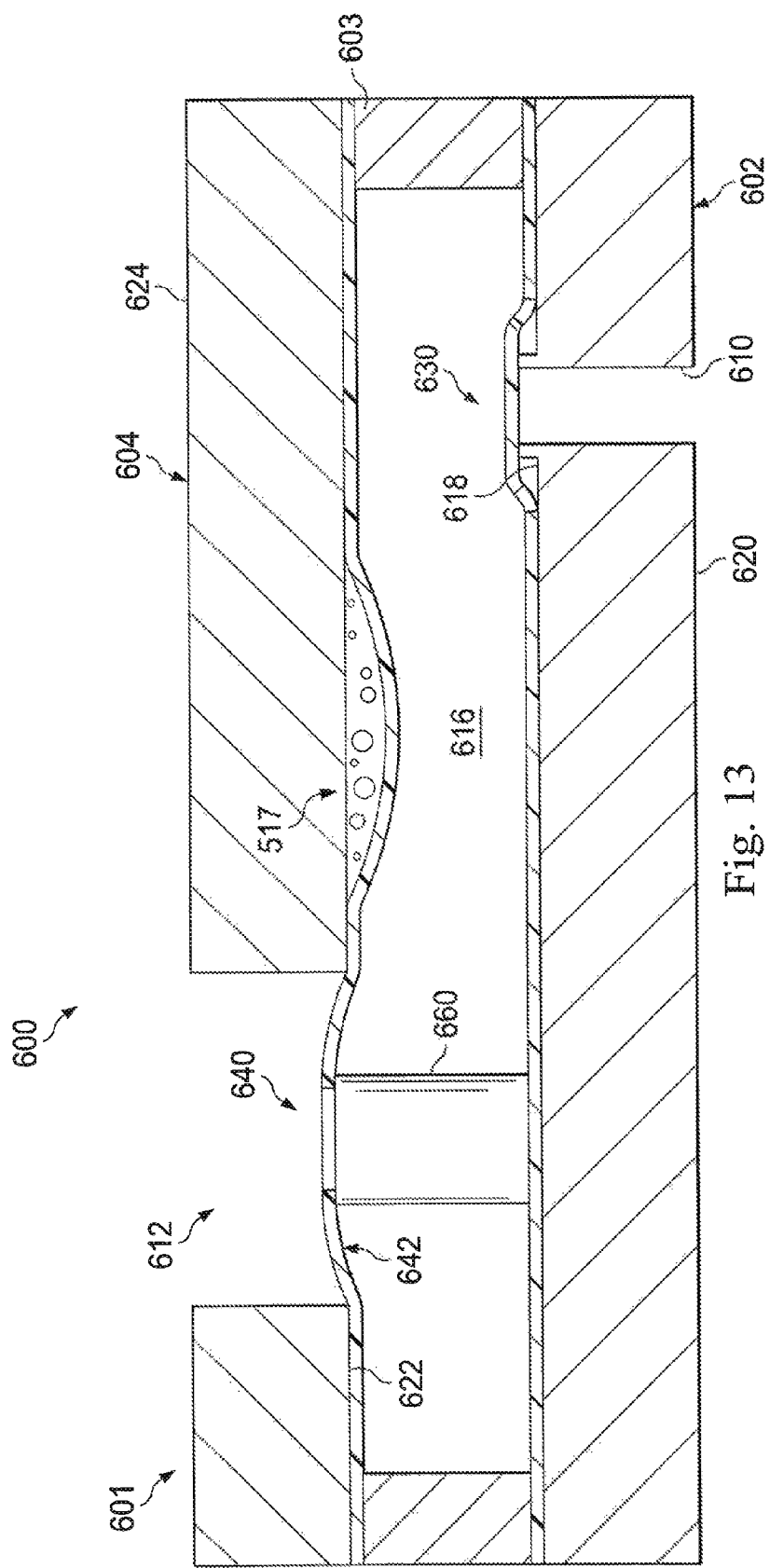
FIG. 13 is a stylized illustration of an exemplary flow system.

As described above, the valve chip 502 and the actuation chip 504 are stacked together and sandwich the wall element 503 between them to form the fluid flow passageway 516. Both the valve chip 502 and the actuation chip 504 may be formed using MEMS technology. In some embodiments, the chips may be silicon wafers. As can be seen in FIG. 5, the valve chip 502 includes an upper side 518 facing the passageway 516 and a lower side 520 opposite the upper side. The actuation chip 504 includes a lower side 522 facing the fluid flow passageway 516 and an upper side 524 opposite the lower side 522. In the embodiment shown, one inlet port 510 and one outlet port 512 extends from the upper side 518 to the lower side 520 of the valve chip 502. In other embodiments, the flow system may include any of a number of inlet ports and outlet ports arranged in a variety of configurations (e.g., as shown in FIG. 13).

The flow system 500 includes an inlet valve 530 and an outlet valve 540. In FIG. 5, the flow system 500 is depicted in an unpressurized condition or state wherein both the inlet valve 530 and the outlet valve 540 are in a closed condition. In the pictured embodiment, the inlet valve 530 is an "out-of-plane" check valve that allows flow into the fluid flow passageway 516. When the pressure at the inlet port 510 (i.e., the pressure sensed by pressure sensor P1) is greater than the pressure within the fluid flow passageway 516 (i.e., the pressure sensed by pressure sensor P2) and high enough to overcome the cracking pressure of the inlet valve 530, fluid from the inlet port 510 can enter the fluid flow passageway 516 through the inlet valve 530. The inlet valve 530 is discussed in further detail below after the description of the outlet valve 540.

The outlet valve 540 is an "in-to-plane" check valve, where the direction of flow through the valve is into the plane of the chip 502. The outlet valve 540 permits fluid to exit the fluid flow passageway 516 for further regulation within other structures or release at the drainage site 360. When the pressure within the fluid flow passageway 516 is greater than the pressure within the outlet port 512 (i.e., the pressure sensed by pressure sensor P4) and high enough to overcome the cracking pressure of the outlet valve 540, fluid from the fluid flow passageway 516 can exit the flow system 500 through the outlet valve 540.

FIG. 6 illustrates a cross-sectional view of a portion of the valve chip 502 containing a flexible, deflectable sealing portion or outlet membrane 542 of the outlet valve 540 in accordance with one embodiment of the disclosure. As shown in FIG. 5, the outlet valve 540 comprises the outlet membrane 542 that spans the outlet port 512 and a valve seat 560. The outlet valve 540 is configured as a flow control valve that can completely or partially block the flow of aqueous humor by deflecting the outlet membrane 542 toward the valve seat 560. In the pictured embodiment, the outlet membrane 542 is disposed on the valve chip 502 to overlie the outlet port 512 in the valve chip 502, and the valve seat 560 is disposed on the actuation chip 504. In other embodiments, an outlet membrane 642 may be disposed on an actuation chip 604 and the valve seat 660 may be positioned on a valve chip 602 with an inlet valve 630 (e.g., as shown in FIG. 13).

The outlet membrane 542 may be formed of an elastically deformable biocompatible material such as, by way of non-limiting example, silicone, silicon nitride, silicone elastomer, polyimide, Parylene, and others. In the example shown, the outlet membrane 542 is secured at its periphery to the upper side 518 of the chip 502. Although shown in cross section, the outlet port 512 may be formed as a cylindrical tube with a circular opening 546. Accordingly, the outlet membrane 542 may be shaped and configured as a generally circular structure that is circumferentially secured to the upper side 518 of the chip 502 a distance apart from the opening 546. As such, as the volume or pressure increases within the fluid flow passageway 516 relative to the pressure within the outlet port 512, a central portion of the outlet membrane 542 provides the highest level of displacement or deflection. In other embodiments, the opening 546 and the outlet membrane 542 are formed so that the membrane has a non-circular shape, including oval, substantially rectangular, or square, for example. Other shapes are also contemplated.

Figure 7:
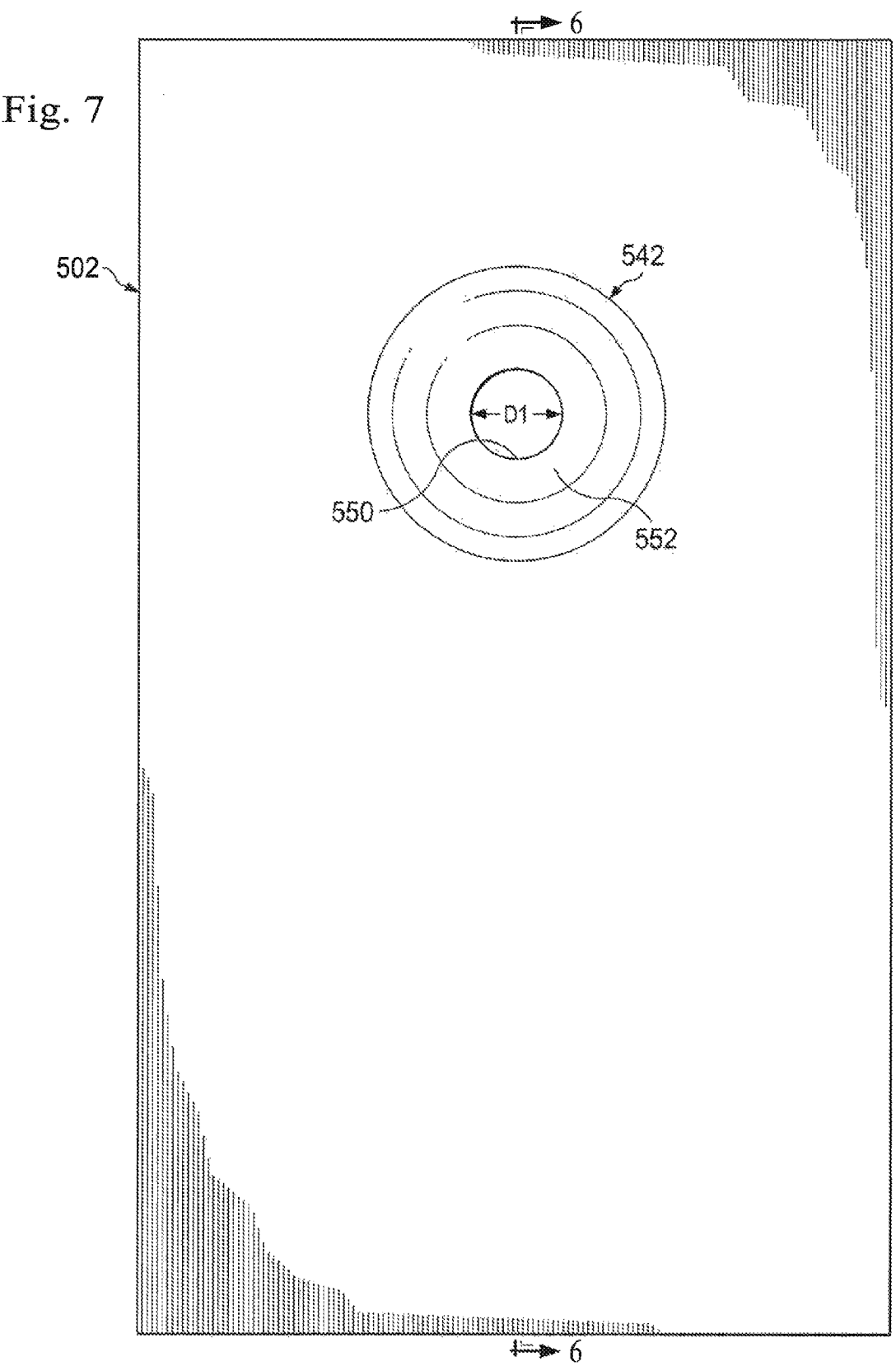
FIG. 7 is a stylized illustration of a top view of the portion of the exemplary valve chip including the exemplary outlet valve shown in FIG. 6.

FIG. 7 illustrates a top view of the portion of the valve chip 502 shown in FIG. 6. As shown in FIGS. 6 and 7, the outlet membrane 542 includes a flow aperture 550 and a sealing portion 552. The flow aperture 550 is formed as a through hole in the outlet membrane 542. The flow aperture 550 has a diameter D1. The diameter D1 may range from 10 μm to 2 mm. In one embodiment, by way of non-limiting example, the diameter D1 is 300 μm. In this embodiment, the flow aperture 550 is disposed in the center of the outlet membrane 542, and the sealing portion 552 is circumferentially disposed around the flow aperture 550. In some embodiments, the flow aperture 550 is formed of a mesh or screen material that permits a fluid to flow therethrough. As used herein, mesh material includes any material having perforations or holes allowing fluid flow therethrough. In various embodiments, the flow aperture 550 may be of any shape and of any size that permits the fluid to pass into the outlet port 512. The shapes and sizes of the membrane 542 and the flow aperture 550 may be chosen depending upon spatial, pressure drop, material, and flow rate constraints.

FIG. 8 illustrates a cross-sectional view of a portion of the actuation chip 504 shown in FIG. 5 in accordance with one embodiment of the disclosure. As shown in FIG. 8, the valve seat 560 is disposed on the lower surface 522 of the actuation chip 504. The valve seat 560 has a contact surface 562. In the pictured embodiment, the valve seat 560 is shaped and configured as a boss member that protrudes into the fluid flow passageway 516 (shown in FIG. 5). A boss member may permit increased design flexibility and flow control for the outlet valve 540. Varying the height and other dimensions of the boss member could affect the pressure required to open the outlet valve 540 and the amount and rate of fluid flow through the outlet valve 540. In other embodiments, the valve seat 560 may be flush with the lower surface 522 of the actuation chip 504. The valve seat 560 is shaped and configured such that when the outlet membrane 542 contacts the valve seat 560, the valve 540 is in a closed condition. Alternatively, the membrane 542 may move sufficiently close to the valve seat 560 to partially close the valve 540 and partially restrict rather than cut off flow.

FIG. 9 illustrates a top view of the portion of the valve chip 504 shown in FIG. 8. In the pictured embodiment, the valve seat 560 is shaped as a cylindrical boss member having the circular, substantially planar contact surface 562. The contact surface 562 has a diameter D2. The diameter D2 is larger than the diameter D1 of the flow aperture 550 such that when the outlet membrane 542 contacts the valve seat 560, flow is obstructed through the outlet valve 512. The diameter D2 may range 10 μm to 2 mm. In one embodiment, by way of non-limiting example, the diameter D2 is 500 μm. In other embodiments, the valve seat 560 may have any of a variety of three dimensional shapes, including, without limitation, cuboid, rectangular prism, rhombohedron, and conical. In other embodiments, the contact surface 562 of the valve seat 560 may have any of a variety of shapes, including, without limitation, rectangular, ovoid, and square. In some embodiments, the contact surface of the valve seat may be nonplanar, such as, by way of non-limiting example, domed, textured, or concave.

In various embodiments, the valve seat 560 may be configured as an integral extension of the actuation chip 504, or may be a separate component. In some examples, the valve seat 560 is an integral portion of the actuation chip 504 and may be printed, molded, or machined at the same time as the actuation feature (i.e., the active component 517). For example, the valve seat 560 may be fabricated by printing or by micromachining or MEMS techniques at the same time, or in processing steps before or after the fabrication of the pump feature, depending on the exact nature of the fabrication process used (such as whether the process steps used for these features are primarily additive or subtractive in nature).

The valve chip 502, the wall element 503, and the actuation chip 504 are shaped and configured such that deflection of the outlet membrane 542 at least partially opens and closes the outlet valve 540 to the outflow of aqueous humor from the flow system 500. As shown in FIG. 5, in one embodiment, the outlet valve 540 is formed by stacking the valve chip 502 shown in FIG. 6 and the actuation chip 504 shown in FIG. 8 such that the outlet membrane 542 of the valve chip 502 can contact the valve seat 560 of the actuation chip 504. The valve seat 560 is positioned relative to the outlet port 512 such that the flow aperture 550 of the outlet membrane and the valve seat 560 are co-aligned about a central axis A. Regardless of how the outlet membrane 542 is secured within the housing 501, at least a portion of the housing 501 is connected to a portion, such as a periphery, of the membrane 542 to maintain it in a desired position relative to the valve seat 560. When the sealing portion 552 of the outlet membrane 542 rests on the valve seat 560, the outlet membrane restricts the flow of fluid from the fluid flow passageway 516 into the outlet port 512, and the outlet valve 540 is in a closed position. If pressure in the fluid flow passageway 516 is greater than the outlet pressure and sufficient to deflect the outlet membrane 542, the outlet membrane 542 may deflect toward the outlet port 512 so that the sealing portion 552 moves away from the valve seat 560 and fluid can exit the fluid flow passageway 516 through the outlet port 512. When the sealing portion 552 lifts away from the valve seat 560, fluid from the fluid flow passageway 516 may flow into the outlet port 512 through the flow aperture 550, and the outlet valve 540 is in an open condition. Thus, the outlet valve 540 may be fabricated on two different chips or substrates, the first of which has a membrane structure and the second of which has a valve seat toward which the membrane may deflect to seal the valve.

As described above, the inlet valve 530 is an "out-of-plane" check valve that allows flow into the fluid flow passageway 516. As shown in FIG. 5, the inlet valve 530 comprises a flexible, deflectable sealing portion or inlet membrane 570 that spans a valve seat 572 of the inlet port 510 on the upper side 518 of the chip 502. The valve 530 is configured as a flow control valve that can completely or partially block the flow of aqueous humor by deflecting the inlet membrane 570 completely or partially across the inlet port 510. In the pictured embodiment, the housing 501 is configured to connect with the drainage tube 330 such that deflection of the inlet membrane 570 at least partially opens and closes the inlet valve 530 to the inflow of aqueous humor through the inlet port 510 into the flow system 500. The valve seat 572 is shaped and configured such that when the inlet membrane 570 rests on the valve seat 572, the valve 530 is in a closed condition. In the pictured embodiment, the valve seat 572 is a raised rim surrounding the inlet port 510 and extending into the fluid flow passageway 516. In other embodiments, the valve seat 572 may be flush with the upper surface 518 of the valve chip 502.

The inlet membrane 570 is formed of an elastically deformable biocompatible material such as, by way of non-limiting example, silicone, silicon nitride, silicone elastomer, polyimide, Parylene, and others. In the example shown, the inlet membrane 570 is a substantially planar membrane secured at its periphery to the upper side 518 of the chip 502. Although shown in cross section, the inlet port 510 may be formed as a cylindrical tube and the valve seat 572 may be circular. Accordingly, the inlet membrane 570 may be shaped and configured as a generally circular structure that is circumferentially secured to the upper side 518 of the chip 502 a distance apart from the valve seat 572. As such, as the volume or pressure increases within the inlet port 510 relative to the pressure within the fluid flow passageway 516, a central portion of the inlet membrane 570 provides the highest level of displacement or deflection. In other embodiments, the seat 572 and the inlet membrane 570 are formed so that the membrane has a non-circular shape, including oval, substantially rectangular, or square, for example. Other shapes are also contemplated. The shape of the membrane 570 may be chosen depending upon spatial, pressure drop, material, and flow rate constraints.

In the embodiment shown, the inlet membrane 570 includes one or more flow apertures 574 and a sealing portion 576. In this embodiment, the flow apertures 574 are disposed off-center, and the sealing portion 576 is disposed in a central region of the inlet membrane 570. If pressure in the inlet port 510 is great enough to overcome the pressure within the fluid flow passageway 516 and any inherent resistance of the valve 530, the inlet membrane 570 may deflect away from the valve seat 572 to allow fluid from the inlet passageway 510 to flow into the fluid flow passageway 516 through the flow apertures 574. If pressure in the fluid flow passageway 516 is greater than the inlet pressure, the inlet membrane 570 may deflect toward the inlet port 510 so that the sealing portion 576 abuts against the valve seat 572 and restricts fluid from entering (or exiting) the fluid flow passageway through the inlet port 510.

The flow apertures 574 are formed as through holes in the inlet membrane 570. In some embodiments, the flow apertures 574 are formed of a mesh or screen material that permits a fluid to flow therethrough. The flow apertures 574 may be of any shape and of any size that permits the fluid to pass into the fluid flow passageway 516. In some embodiments, the inlet membrane 570 includes a solid central portion and the flow apertures, such as a screen or porous material, forms the entire periphery of the inlet membrane 570. Other arrangements are also contemplated.

For purposes of practicality, the membranes 542, 570 should be thick enough to be durable and resistant to corrosion and leakage. However, the membranes 542, 570 should also be thin enough to provide the necessary flexibility and deflection capabilities which are required in a substantially planar membrane designed for use in a pressure-responsive IOP control system. A preferred thickness of the membranes 542, 570 will depend on the deflection response desired for a given pressure and the material chosen. As an example, the membrane 542 may be fabricated out of Parylene and may have a thickness ranging from 0.5 µm to 30 µm. The membrane 570 may have a similar thickness and material as membrane 542, or for the sake of illustrating a different choice, it could be made of silicon and have a thickness ranging from 0.3 µm to 10 µm. In some embodiments, the membranes are substantially flat, without corrugation features. In some embodiments, any one or both of the membranes 542, 570 may include annular corrugations (such as ridges and valleys) whose depths affect the deflection profile of the membrane in response to various pressures. The thickness, material, and diameter of the membranes 542, 570, as well as the depth, number, and orientation of the corrugations, may all affect the cracking pressure and deflection profiles of the membranes.

In some embodiments, the membranes 542, 570 can be fabricated integrally on the valve chip 502 with some or all of the housing features by micromachining or MEMS techniques as are well known in the art using a series of material deposition, lithographic patterning and etching steps on suitable substrates. As an example, a suitable substrate that may form the valve chip 502 or the actuation chip 504 may use a Si or glass wafer as a starting point, with various spacing layers of Silicon, glass, dielectric, or spin-on materials to form parts of the housing, and a flexible membrane material such as thinned silicon, silicon nitride, compliant metal such as gold, or biocompatible organic materials such as Parylene, silicone rubber, PDMS or the like, alone or in combination, in suitable thicknesses and dimensions to yield the desired performance. In some embodiments, the membranes 542, 570 can be fabricated as one continuous membrane atop the valve chip 502 (i.e., deposited continuously across the upper side 518 of the valve chip 502). This continuous layer of flexible material can then be left intact or separated into two discrete membranes 542, 570 by selective removal of the flexible material. In some embodiments, the membranes 542, 570 can be fabricated as two discrete membranes. In some embodiments, the membranes 542, 570 can be fabricated from dissimilar materials Thus, the inlet valve 530 and the membrane portion of the outlet valve 540 are formed on the same side of a single chip (i.e., the upper side 518 of the valve chip 502). Accordingly, even with two check valves arranged to restrict flow in opposite directions, the flow system 500 can be constructed with only two chips and the necessary MEMS manufacturing processes to fabricate the two check valves may be performed on the same side of a single chip. To create a pump having two out-of-plane check valves as an inlet an outlet valve, it is typically necessary to use two chips each with a single check valve attached back-to-back or one chip that has been fabricated with MEMS features on both sides. Valves using the former approach would require at least 3 chips to achieve the desired functionality, and valves using the latter approach often require a costly and complicated fabrication process. Because of the disclosed structure of the outlet valve 540 and the resultant arrangement of the inlet and outlet valves on the same side of the chip 502, the desired pump functionality may be achieved using only the two chips 502 and 504, whereas devices using two out-of-plane check valves would typically use at least one additional chip. Thus, the configuration of the outlet valve 540 disclosed herein can reduce the stack size and/or the cost of manufacturing required to carry out the operation of the flow system 500.

The cracking pressure of a valve generally refers to the minimum pressure differential needed between the entrance and exit of the valve to lift the membrane off its valve seat. The cracking pressure of the outlet valve 540 is dependent upon the structure and configuration of the membrane 542 and structure and configuration of the valve seat 560. In the described embodiment, the membrane 542 is shaped and configured to contact the valve seat 560 in an unpressurized condition, as shown in FIG. 5. In particular, the outlet membrane 542 is shaped and configured to be pre-biased over the valve seat 560 in a neutral, unpressurized state.

If the pressure differential P2:P4 across the outlet membrane 542 is greater than the cracking pressure of the outlet valve 540, then the outlet membrane 542 will deflect away from the contact surface 562 of the valve seat 560 further into the outlet port 512, and the outlet valve 540 will assume an open condition. When the outlet valve 540 is in an open condition, aqueous fluid flows through the outlet valve 540. The distance of deflection of the outlet membrane 542 away from the valve seat 560 depends at least partially upon the degree by which the pressure differential P2:P4 across the outlet membrane 542 is greater than the cracking pressure of the outlet valve 540. Thus, the outlet valve 540 may assume varying degrees of an open state or open condition.

If the pressure differential P2:P4 across the outlet membrane 542 is less than the cracking pressure of the outlet valve 540, then the outlet membrane 542 will remain in contact with the contact surface 562 of the valve seat 560, and the outlet valve 540 will remain in or assume a closed condition. When the outlet valve 540 is in a closed condition, aqueous fluid cannot flow through the outlet valve 540. In particular, the outlet valve 540 will not open to allow aqueous humor to drain into the drainage site 360 unless the pressure differential across the valve 540 (P2:P4) overcomes the cracking pressure of the outlet valve 540.

The cracking pressure of the outlet valve 540 is dependent upon the structural characteristics of the outlet membrane 542 and the valve seat 560. Therefore, the cracking pressure of the outlet valve 540 is dependent upon the geometry (e.g., shape, diameter, and thickness), and material properties (e.g., stiffness) of the membrane 542 as well as the geometry (e.g., size and shape), and material properties (e.g., stiffness) of the valve seat 560. For example, the specific configuration and structure of the outlet valve 540 (e.g., the height of the valve seat 560 and the diameter of outlet membrane 542, by way of non-limiting example) can be selected to create a particular cracking pressure for the valve. Thus, the in-to-plane outlet valve 540 can incorporate a substantial cracking pressure for the flow system 500, which can assist in the clinical management of hypotony associated with glaucoma drainage devices. Accordingly, the cracking pressure of the outlet valve 540 may be preselected by controlling these parameters during the manufacturing or assembly processes. In addition, the healthcare provider may select a flow system including a valve having a particular cracking pressure based on the most appropriate or desired IOP range for the treatment of a particular condition. For example, in the pictured embodiment, the raised, boss-like structure of the valve seat 560 increases the cracking pressure of the outlet valve 540 by increasing the pre-bias of the membrane, thereby raising the pressure differential P2:P4 required for the outlet valve 540 to assume an open condition.

Figure 10:
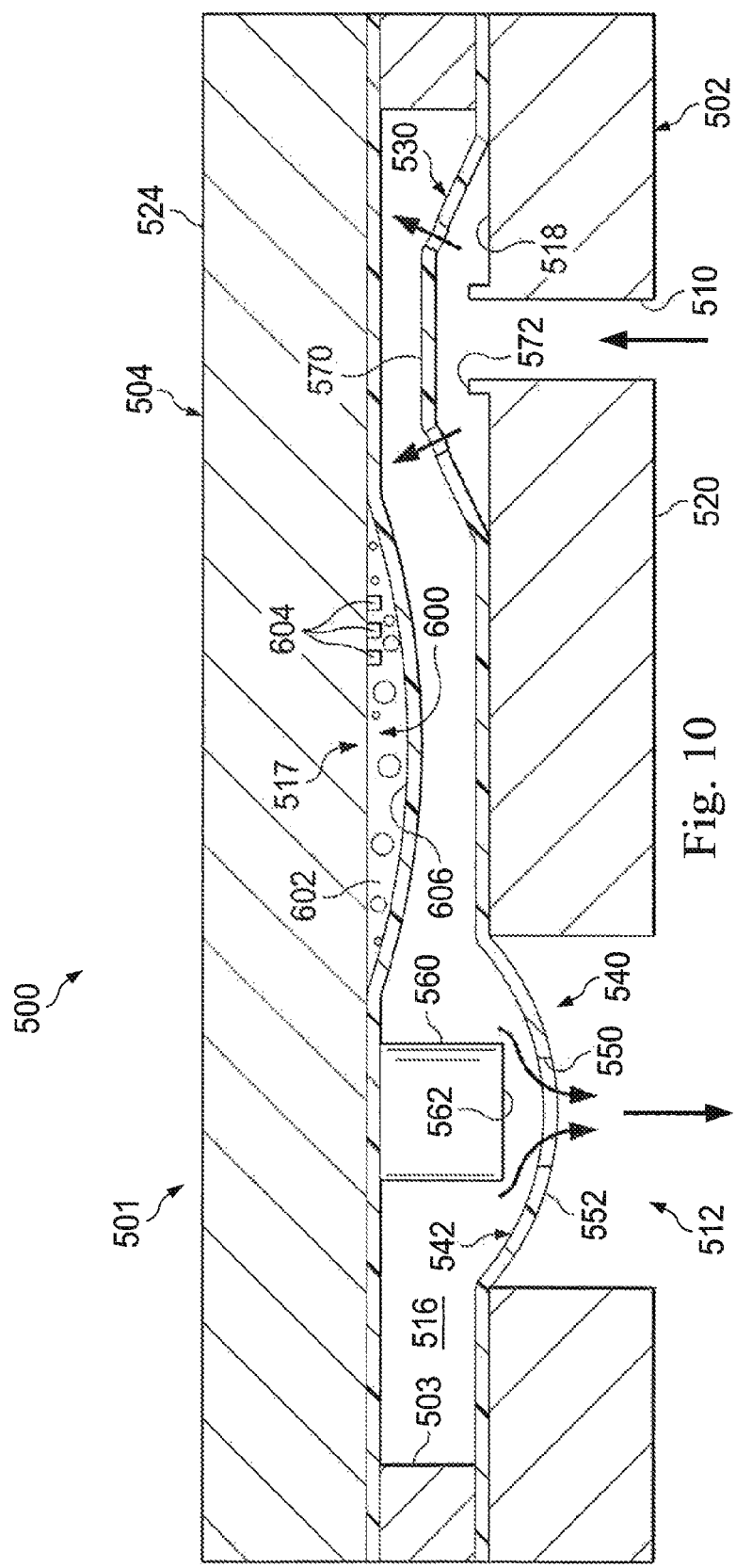
FIG. 10 is a stylized illustration of a cross-sectional view of the exemplary flow system shown in FIG. 5 in an open, flow-permitting condition according to one embodiment consistent with the principles of the present disclosure, where both the inlet valve and the outlet valve are in an open condition.

FIG. 10 illustrates the flow system 500 in an open, flow-permitting condition, where both the inlet valve 530 and the outlet valve 540 are in open conditions. The flow system 500 may assume this condition in a high upstream pressure state where the anterior chamber pressure (e.g., as measured by IOP sensor P1) is sufficiently high to overcome the summation of the cracking pressures of both the inlet valve 530 and the outlet valve 540, thereby causing both the inlet valve 530 and the outlet valve 540 to assume open conditions.

As shown in FIG. 10, the actuation chip 504 includes the active component 517 usable to create a pumping action in the flow system 500. In the pictured embodiment, the active component 517 is an electrolytic actuator comprising a flow control chamber 600, actuator fluid 602, electrodes 604 arranged to cooperate with the actuator fluid 602, and a flexible membrane 606. The chamber 600 is sealed closed and separated from the fluid flow passageway 516 by the membrane 606. Accordingly, as pressure increases within the chamber 600, the membrane 606 displaces in the direction of the fluid flow passageway 516.

The actuator fluid 602 is contained in the flow control chamber 600 and includes, in some embodiments, water. Some embodiments include a saline such as sodium chloride in solution or other salts. Other embodiments include other forms of electrolytes such as sulfuric acid, sodium bicarbonate, potassium nitrate, lithium sulfate, copper sulfate, magnesium sulfate and others.

The electrodes 604 are disposed within the actuator fluid 602 in a manner permitting at least a portion of the ions and electrolytes in the actuator fluid 602 to phase change from liquid to gas, forming gas bubbles through electrolysis. As the bubbles form, the pressure in the chamber 600 increases. This increased pressure acts on the membrane 606 to cause its displacement toward the valve chip 502, displacing volume and increasing pressure within the flow passage 516. The electrodes 604 are in electrical communication with the power source 205, which is controlled by the processor 215 (shown in FIG. 3).

The membrane 606 comprises a flexible, deformable, fluid-tight membrane or diaphragm anchored to the actuation chip 504. The membrane 606 can deflect in response to pressure differentials across its opposing sides. The membrane 606 can be formed of any suitable biocompatible material that can move, flex, deform, or deflect in response to pressure. In some embodiments, the membrane 606 is constructed of a micro-electromechanical system (MEMS) membrane, such as, but not by way of limitation, a Parylene membrane.

In another example, instead of having the active component 517 disposed on the actuation chip 504, the active component is disposed on the upper side 518 of the valve chip 502. Accordingly, in this embodiment, all the displaceable members and/or membranes are formed on the same chip reducing the quantity of chips with flexible material processes.

The IOP control system is configured to adjust the flow through the flow system 500 based on measured pressure values or derivatives from the pressure sensors. If the pressures are not within desired ranges, the IOP control system 200 may adjust the flow system 500 to increase or decrease drainage flow through the drainage tube 330 to effect a pressure change to the desired pressure. To do this, the processor 215 operates the flow system 500 with the power source 205 to activate or deactivate the electrodes 604 in the flow system 500 and/or the other structures. The electrodes 604 act within the actuator fluid 602 to change at least a portion of the fluid to a gaseous state, increasing the pressure and likewise the volume within the flow control chamber 600, causing the membrane 606 to expand into the flow passage 516, displacing volume and increasing pressure within the flow passage 516. Over time these molecules recombine to change into a fluid state, decreasing the pressure and likewise the volume within the flow control chamber 600. The pressure and the volume changes within the flow passage 516 affect the position of the membranes 542, 570 relative to the valve seats 560, 572, respectively, thereby influencing whether the valves 540, 530, respectively, are in the open or closed condition.

In FIG. 10, as described above, the flow system 500 is in an open condition, allowing the passive, unpowered flow-through of aqueous humor from the inlet port 510, through the fluid flow passageway 516, and out the outlet port 512 in a high upstream pressure state. When the pressure of fluid within the inlet port 510 (i.e., the pressure sensed by sensor P1) is sufficiently greater than the combined cracking pressures of the inlet valve 530 and the outlet valve 540, the inlet valve 530 and the outlet valve 540 may assume an open condition.

In this high upstream pressure state, the pressure differentials within the flow system 500 allow the membranes 570, 542 to lift away from the valve seats 572, 560, respectively, and allow the passage of aqueous humor through the flow system. As described above, the positions of the membranes 570, 542 relative to the valve seats 572, 560, respectively, determine whether the valves 530, 540, respectively, are in the open or closed condition. When the membrane 542 deflects away from the valve seat 560 into the outlet port 512, as shown in FIG. 10, fluid may exit the fluid flow passageway 516 through the flow aperture 550, and the valve 540 is in an open condition. In particular, the sealing portion 552 extends into the outlet port 512 (i.e., into the body or plane of the valve chip 502) to allow fluid to flow from the fluid flow passageway 516 into the outlet port 512. Conversely, when the sealing portion 552 of the membrane 542 abuts the contact surface 562 of the valve seat 560, the outlet valve 540 is in a closed condition, as shown in FIG. 12.

Figure 11:
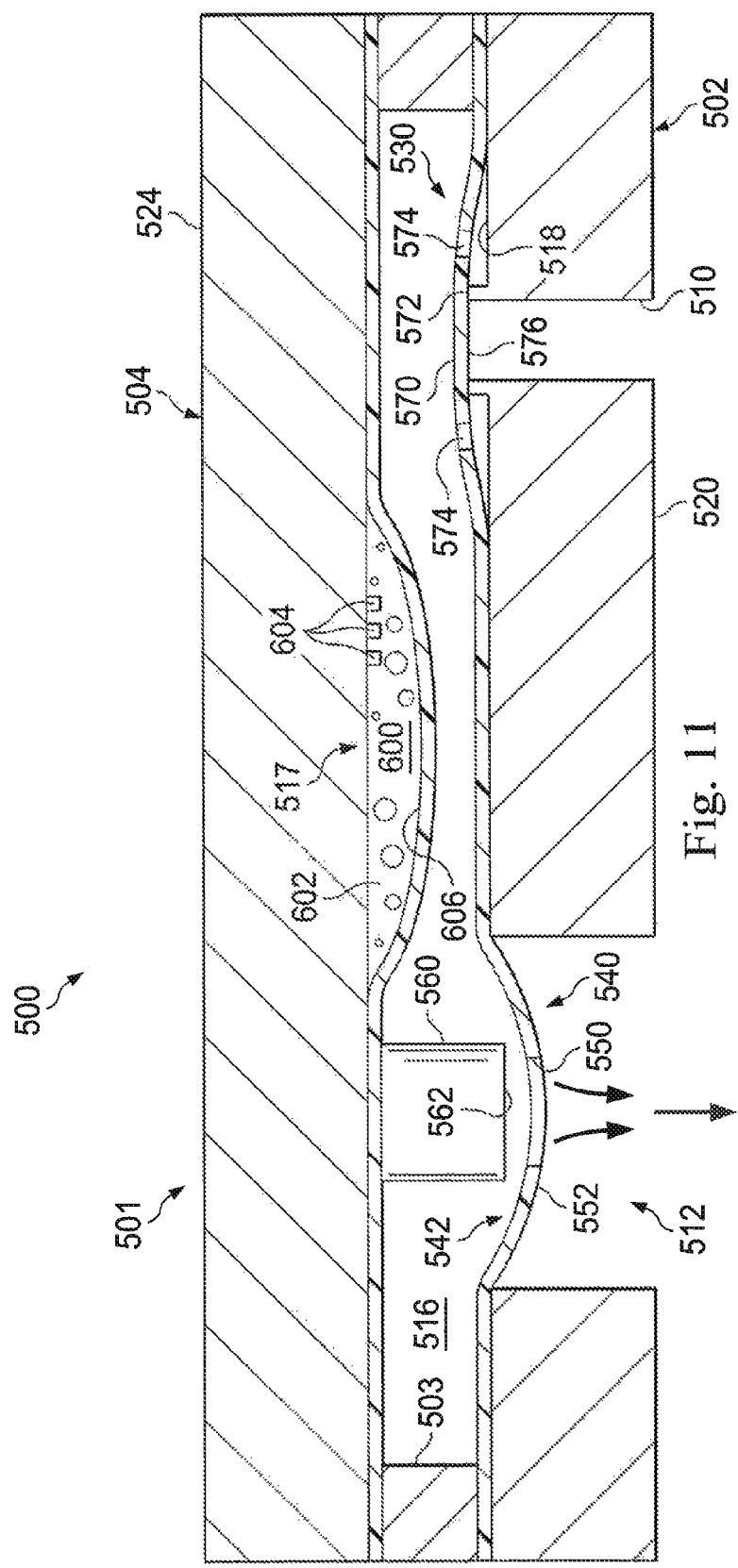
FIG. 11 is a stylized illustration of the exemplary flow system shown in FIG. 10 where the inlet valve is in a closed condition and the outlet valve is in an open condition.

FIG. 11 illustrates the flow system 500 in a partially open condition, wherein fluid is permitted to exit the fluid flow passageway 516 through the outlet valve 540, but fluid is prevented from entering (or exiting) the fluid flow passageway through the inlet valve 530. In the pictured scenario, the active component 517 is in an expanding or inflating condition as the volume within the flow control chamber 600 increases and the membrane 606 moves toward the valve chip 502. In particular, voltage applied across the electrodes 604 causes the phase change through electrolysis of a portion of the actuator fluid 602 to generate gas bubbles in the actuator fluid, increasing the volume within the flow control chamber 600. In particular, as the actuator fluid 602 in the flow control chamber 600 enters a gaseous state, the volume in the flow control chamber increases, causing the flexible membrane 606 to deflect further into the fluid flow passageway 516. This causes the pressure in the fluid flow passageway 516 (i.e., the pressure measured by sensor P2) to increase and the outlet valve 540 transitions into the open position as the inlet check valve 530 transitions into the closed position.

As the pressure in fluid flow passageway 516 increases, any fluid in the fluid flow passageway is restricted from moving though the inlet port by the inlet valve 530, which moves into a closed position due to the increased pressure in fluid flow passageway relative to the pressure within the inlet port (i.e., the pressure measured by pressure sensor P1). In particular, the sealing portion 576 of the inlet membrane 570 of the inlet valve 530 moves toward the inlet port 510 to abut the valve seat 572, thereby preventing fluid from the fluid flow passageway 516 to exit the fluid flow passageway 516 through the inlet port 510. Meanwhile, the fluid in the fluid flow passageway 516 exits the flow system 500 through the flow aperture 550 of the outlet valve 540 due to the pressure increase in fluid flow passageway relative to the pressure within the outlet port (i.e., the pressure measured by pressure sensor P4), which acts on the outlet valve to move it into the open position by moving the outlet membrane 542 away from the valve seat 560. In particular, the sealing portion 552 of the outlet membrane 542 moves into the outlet port 512 (i.e., into the plane of the valve chip 502) until the outlet membrane is no longer in contact with the contact surface 562 of the valve seat 560, thereby allowing the egress of fluid from the fluid flow passageway 516. In the situation depicted in FIG. 11, the outlet valve 540 is in an open position because the pressure within the fluid flow chamber 516 (the pressure measured by the sensor P2) is greater than and overcomes the cracking pressure of the valve 540 (the pressure difference P2:P4 required to lift the outlet membrane 542 from the contact surface 562 of the valve seat 560). The arrows in FIG. 11 indicate the path of fluid flow from the fluid flow passageway 516 through the outlet valve 540.

Figure 12:
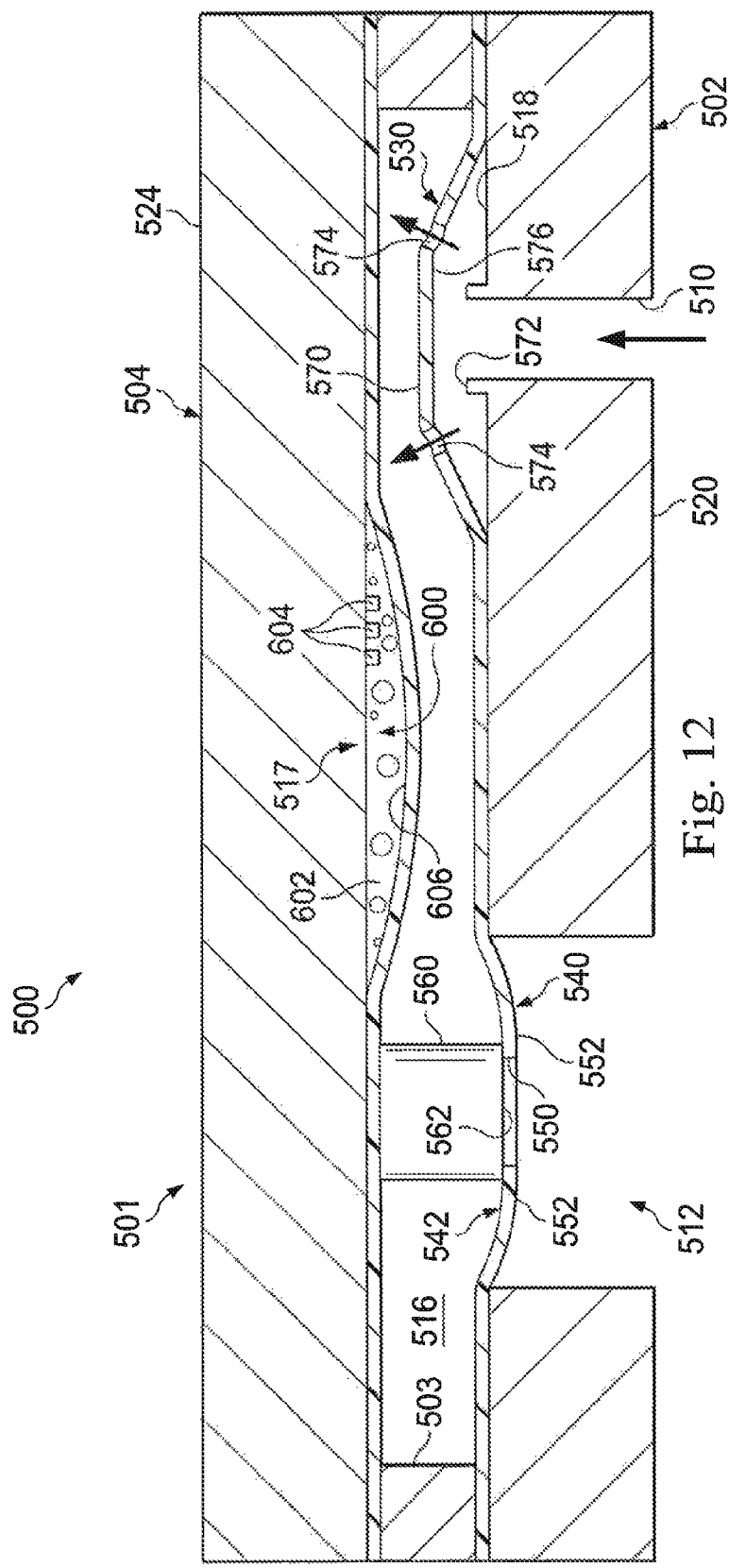
FIG. 12 is a stylized illustration of the exemplary flow system shown in FIG. 10 where the inlet valve is in an open condition and the outlet valve is in a closed condition.

FIG. 12 illustrates the flow system 500 in a partially opened condition, wherein fluid is permitted to enter the fluid flow passageway 516 through the inlet valve 530, but fluid is prevented from exiting the fluid flow passageway through the outlet valve 540. In the situation depicted in FIG. 12, the outlet valve 540 is in a closed position because the pressure within the fluid flow passageway 516 (the pressure measured by sensor P2) is less than and does not overcome the cracking pressure of the valve 540 (the pressure difference P2:P4 required to lift the outlet membrane 542 from the contact surface 562 of the valve seat 560). In the pictured scenario, the active component 517 is in an unexpanding or deflating condition as the volume within the flow control chamber 600 decreases and the membrane 606 moves toward the actuation chip 504. In particular, as the gas in the flow control chamber 600 returns to its liquid state, the volume in the flow control chamber decreases, causing the flexible membrane 606 to move further out of the fluid flow passageway 516. This causes the pressure in the fluid flow passageway 516 (i.e., the pressure measured by the sensor P2) to decrease and the outlet valve 540 to transition into the closed position as the inlet check valve 530 transitions into the open position. The membrane 542 moves toward the actuation chip 504 until the sealing portion 552 abuts the contact surface 562 of the valve seat 560, thereby halting the egress of fluid from the fluid flow passageway 516. Meanwhile, the sealing portion 576 of the membrane 570 of the inlet valve 530 lifts off the valve seat 572 toward the fluid flow passageway 516, allowing fluid from the inlet port 510 to enter the fluid flow passageway through the flow apertures 574. The processes described in FIGS. 11 and 12 can be repeated cyclically to move fluid through the flow system 500 in a pumping manner.

FIG. 13 shows a stylized cross-sectional view of an exemplary flow system 600 carried by or forming a part of the plate 172 (shown in FIG. 2). The flow system 600 may be substituted for the flow system 230 and therefore, the discussion above applies equally to the flow system 600. The flow system 600 is configured to selectively allow or block or drive aqueous humor flowing from the anterior chamber 350 through the drainage tube 330 to the drainage site 360 (shown in FIG. 4) or to any subsequent flow control structures such as, by way of non-limiting example, valves, pumps, and/or check valves before entering the drainage site. The flow system 600 is substantially similar to the flow system 500 described above in relation to FIGS. 5-12 except for the differences described or shown.

The flow system 600 comprises a housing 601 including a valve chip 602, a wall element 603, and an actuation chip 604. In FIG. 13, for illustrative clarity, the valve chip 602 and the actuation chip 604 are shown arranged farther apart from each other than may actually occur. In addition, the flow system 600 comprises an inlet port 610, an outlet port 612, a fluid flow passageway 616 extending between the inlet port 610 and the outlet port 612, and the active component 517. The valve chip 602, the wall element 603, and the actuation chip 604 are shaped and configured to mate and create the fluid flow passageway 616. In some embodiments, the valve chip 602 and the actuation chip 604 are shaped to directly connect to one another to create an enclosed fluid flow passageway without the need for a separate wall element. In this example, the flow system 600 is a pump configured to draw fluid into the fluid flow passageway 616 through the inlet port 610 and expel the fluid from the fluid flow passageway 616 through the outlet port 612. The inlet port 610 may be in fluid communication with the drainage tube 330 (shown in FIG. 4) and is configured to receive aqueous humor flowing from the drainage tube 330 into the fluid flow passageway 616. The outlet port 612 permits fluid to exit the fluid flow passageway 616 for release at a drainage site or for further regulation via additional flow systems.

As described above in relation to the flow system 500 depicted in FIG. 5, the valve chip 602 and the actuation chip 604 are stacked together and sandwich the wall element 603 between them to form the fluid flow passageway 616. Both the valve chip 602 and the actuation chip 604 may be formed using MEMS technology. In some embodiments, the chips may be silicon wafers. As can be seen in FIG. 13, the valve chip 602 includes an upper side 618 facing the passageway 616 and a lower side 620 opposite the upper side 618. The actuation chip 604 includes a lower side 622 facing the fluid flow passageway 616 and an upper side 624 opposite the lower side 622. In the embodiment shown in FIG. 13, the inlet port 610 and the outlet port 612 are disposed on different chips. In particular, the inlet port 610 extends from the upper side 618 to the lower side 620 of the valve chip 602, and the outlet port 612 extends from the upper side 624 to the lower side 622 of the actuation chip 604. Other embodiments may include any number of inlet and outlet ports.

The flow system 600 includes an inlet valve 630 and an outlet valve 640. In FIG. 13, the flow system 600 is shown with both the inlet valve 630 and the outlet valve 640 in the closed condition. The inlet valve 630 may be the same as the inlet valve 530 described above in relation to FIGS. 5-12. The inlet valve 630 is disposed on the valve chip 602. The outlet valve 640 permits fluid to exit the fluid flow passageway 616 for further regulation within other structures or release at the drainage site 360. When the pressure within the fluid flow passageway 616 is greater than the pressure within the outlet port 612 (i.e., the pressure sensed by pressure sensor P4) and high enough to overcome the cracking pressure of the outlet valve 640, fluid from the fluid flow passageway 616 can exit the flow system 600 through the outlet valve 640.

The outlet valve 640 is substantially similar to the outlet valve 540 described above with respect to FIGS. 5-12 except for the differences described or shown. In particular, in the pictured embodiment, an outlet membrane 642 is disposed on the actuation chip 604 to overlie the outlet port 612, and the valve seat 660 is disposed on the valve chip 602 (on the upper side 618 along with the inlet valve 630). In other embodiments, the inlet valve 630 may be disposed on the same chip as both the active component 517 and the outlet valve 640.

The outlet valve 640 is an "in-to-plane" check valve comprising the outlet membrane 642 that spans the outlet port 612 and the valve seat 660, and the direction of flow through the outlet valve 640 is into the plane of the actuation chip 604. The outlet valve 640 is configured as a flow control valve that can completely or partially block the flow of aqueous humor by deflecting the outlet membrane 642 toward the valve seat 660 disposed on the valve chip 602. Thus, in operation, the flow system 600 responds to pressure changes in a similar way to that described above with respect to FIGS. 10-12.

The devices, systems, and methods described herein achieve IOP control with a relatively small and less expensive device than the devices typically used with the same valve functionality. The electrolysis-based system accomplishes this using electrolysis and flexible membranes to affect drainage flow. The exemplary system herein can also take into account intraocular pressures and bleb pressures in regulating drainage flow. It is worth noting that for biocompatibility, the devices disclosed herein may be coated or encapsulated in a material such as polypropylene, silicon, silicone, Parylene, or other materials.

In particular, the MEMS outlet check valve disclosed herein creates new opportunities for creating flow systems, such as a fluid valve or a pump system, in a smaller and/or thinner package. The pre-biased membrane feature of the in-to-plane MEMS outlet check valve allows the flow system to have a substantial cracking pressure to help guard against hypotony, which can be complication of implantable IOP control systems. Also, the unique design of the MEMS outlet check valve allows the outlet check valve to be formed on the same side of a chip as the inlet valve and/or a membranous pump feature. Accordingly, an entire chip layer may be eliminated from the flow system, resulting in a shorter stack of chips for the flow system. This may result in a thinner implant that will likely be more comfortable for the patient. In addition, because the complex material deposition and associated processing necessary to construct the flow system may be performed on a single side of the chip as opposed to opposite sides of the same chip, the overall manufacturing process may be simplified and costs may be reduced.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An IOP control device for implantation in an eye of a patient, comprising:
    a first chip including:
        a first side and an opposing second side; and
        an outlet port extending from the first side to the second side and sized to permit fluid flow therethrough from the first side to the second side;
    a second chip having an outer side and an inner side, wherein the first chip and the second chip stack to form a fluid flow passageway between the first side of the first chip and the inner side of the second chip, the fluid flow passageway having a fluid flow passageway pressure;
    an inlet valve comprising a flexible inlet membrane, the flexible inlet membrane being movable between a closed position inhibiting fluid flow and an open position permitting fluid flow through the inlet valve; and
    an outlet valve comprising a flexible outlet membrane anchored to the first side of the first chip to overlie the outlet port, the outlet membrane including at least one outlet aperture sized to permit fluid flow therethrough and a sealing portion, the sealing portion being movable between a closed position wherein the sealing portion deflects away from the second side toward fluid flow passageway to inhibit fluid flow through the outlet aperture and an open position wherein the sealing portion displaces into the outlet port toward the second side to permit fluid flow through the outlet aperture.

2. The IOP control device of claim 1, further comprising an outlet valve seat on the inner side of the second chip.

3. The IOP control device of claim 2, wherein the sealing portion of the outlet membrane is configured to deflect away from the second side of the first chip and selectively seal against the outlet valve seat and inhibit fluid flow through the outlet aperture when the outlet membrane is in a closed position.

4. The IOP control device of claim 2, wherein the flexible outlet membrane and the outlet valve seat are arranged to pre-bias the flexible outlet membrane over the outlet valve seat in a closed position when the outlet valve is in an unpressurized state.

5. The IOP control device of claim 2, wherein the outlet valve seat and the outlet aperture are aligned about a central axis extending through the valve seat.

6. The IOP control device of claim 2, wherein the outlet valve seat comprises a raised boss element.

7. The IOP control device of claim 6, wherein the raised boss element includes a diameter greater than a diameter of the outlet aperture.

8. The IOP control device of claim 1, further comprising an active component within the fluid flow passageway configured to affect fluid flow through the fluid flow passageway from the inlet port to the outlet port.

9. The IOP control device of claim 8, wherein the active component comprises an electrolytic actuator comprising a flow control chamber configured to contain a gas creating a flow control chamber pressure, an actuator fluid, an electrolysis system configured to affect the flow control chamber pressure by converting at least a portion of the actuator fluid to the gas, and a membrane configured to affect flow through the fluid flow passageway from the inlet port to the outlet port by deflecting in response to pressure differentials of the flow control chamber pressure and the fluid flow passageway pressure acting on opposing sides of the membrane.

10. The IOP control device of claim 1, wherein the flexible outlet membrane comprises an annular membrane with the outlet aperture positioned centrally in the membrane and the sealing portion encircles the outlet aperture.

11. The IOP control device of claim 1, further comprising an inlet port extending from the first side to the second side of the first chip and sized to permit fluid flow therethrough, wherein the flexible inlet membrane is disposed on the first side of the first chip.

12. The IOP control device of claim 1, further comprising an inlet port extending from the inner side to the outer side of the second chip and sized to permit fluid flow therethrough, wherein the flexible inlet membrane is disposed on the inner side of the second chip.

* * * * *